United States Patent
Kim et al.

(10) Patent No.: US 11,998,530 B2
(45) Date of Patent: Jun. 4, 2024

(54) MICELLE COMPRISING BENZIMIDAZOLE-CARBOHYDRATE CONJUGATE COMPOUND, PREPARATION METHOD THEREOF AND USE THEREOF AS ANTICANCER AGENT OR ANTIVIRAL AGENT COMPRISING THE SAME

(71) Applicant: BIOMETRIX TECHNOLOGY INC, Gangwon-do (KR)

(72) Inventors: Taisun Kim, Gangwon-do (KR); Keumsoo Song, Gangwon-do (KR); Junghun Kim, Seoul (KR)

(73) Assignee: BIOMETRIX TECHNOLOGY INC., Gangwon-Do (KR)

( * ) Notice: Subject to any disclaimer, the term of this patent is extended or adjusted under 35 U.S.C. 154(b) by 0 days.

(21) Appl. No.: 17/544,514

(22) Filed: Dec. 7, 2021

(65) Prior Publication Data
US 2023/0248702 A1 Aug. 10, 2023

(30) Foreign Application Priority Data

Aug. 27, 2021 (KR) .................. 10-2021-0114230

(51) Int. Cl.
| A61K 31/4184 | (2006.01) |
| A61K 9/107 | (2006.01) |
| A61K 47/54 | (2017.01) |
| A61P 35/00 | (2006.01) |

(52) U.S. Cl.
CPC ........ *A61K 31/4184* (2013.01); *A61K 9/1075* (2013.01); *A61K 47/549* (2017.08); *A61P 35/00* (2018.01)

(58) Field of Classification Search
CPC ................ A61K 9/1075; A61K 47/549; A61K 31/4184; A61P 35/00
See application file for complete search history.

(56) References Cited

U.S. PATENT DOCUMENTS

| 5,767,138 A | 6/1998 | Camden |
| 6,245,789 B1 | 6/2001 | Camden |
| 6,455,506 B1 | 9/2002 | Townsend et al. |
| 9,527,839 B2 * | 12/2016 | Apgar .................. C07D 405/14 |
| 9,540,364 B2 * | 1/2017 | Apgar .................. A61K 31/427 |
| 2003/0119761 A1 | 6/2003 | Christian |

FOREIGN PATENT DOCUMENTS

| CN | 1181010 A | 5/1998 |
| CN | 1272113 A | 11/2000 |
| CN | 1301158 A | 6/2001 |
| EP | 2322512 A1 | 5/2011 |
| EP | 3907230 A1 | 11/2021 |
| JP | H01104047 A | 4/1989 |
| KR | 10-2005-0016527 A | 2/2005 |
| KR | 20210075895 A | 6/2021 |
| WO | WO1998/051304 | 11/1998 |
| WO | WO1998/056761 | 12/1998 |
| WO | WO 9951619 A | 10/1999 |
| WO | WO2005/058870 | 6/2005 |
| WO | WO 2021/201352 A1 | 10/2021 |
| WO | WO 2021//261663 A1 | 12/2021 |
| WO | WO2021261663 A1 | 12/2021 |

OTHER PUBLICATIONS

Bahrami, K. et al., "Synthesis of 1,2-disubstituted benzimidazoles, 2-substituted benzimidazoles and 2-substituted benzothiazoles in SDS micelles," Green Chemistry, vol. 12, pp. 1237-1241, May 2010. 5 pages.

Umara, V.D. et al., "Synthesis of Benzimidazoly1-6-aminoββββ-D-glucopyranoses," Asian Journal of Chemistry, vol. 20, No. 7, Sep. 2008. 7 pages.

Sallam, M. et al., "Studies on saccharide benzimidazoles: 2-(β-D-gulofuranosyl)benzimidazole and 2-(β-D-glucofuranosyl)benzimidazole C-nucleoside analogs; synthesis, anomeric configuration and antifouling potency," Carbohydrate Research, vol. 496, Oct. 2020. 27 pages.

Umare, V.D. et al.; "Synthesis of Benzimidazoly1-6-amino-β-D-glucopyranoses"; Asian Journal of Chemistry, vol. 20, No. 7; Sep. 2008. 7 pages.

Sallam, M. et al.; "Studies on saccharide benzimidazoles: 2-(β-D-gulofuranosyl)benzimidazole and 2-(β-D-glucofuranosyl) benzimidazole C-nucleoside analogs; synthesis, anomeric configuration and antifouling potency"; Carbohydrate Research, vol. 496; Oct. 2020; 12 pages.

Panwar, Preety et al.; "Preparation, characterization, and in vitro release study of albendazole-encapsulate nanosize liposomes"; International Journal of Nanomedicine; Feb. 26, 2010; 8 pages.

Extended European Search Report; European Patent Office; Application No. 21213083.5; dated Jun. 3, 2022; 9 pages.

(Continued)

*Primary Examiner* — Pancham Bakshi
(74) *Attorney, Agent, or Firm* — George S. Blasiak; HESLIN ROTHENBERG FARLEY & MESITI P.C.

(57) ABSTRACT

Disclosed herein are a micelle comprising a benzimidazole-carbohydrate conjugate compound represented by the following chemical formula 1, a preparation method thereof, and use thereof as an anticancer agent or an antiviral agent comprising the same:

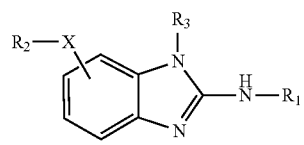

[Chemical formula 1]

in the above formula, $R_1$, $R_2$, $R_3$ and X are the same as those defined in the disclosure and claims.

12 Claims, 20 Drawing Sheets

(56) References Cited

OTHER PUBLICATIONS

International Search Report; Application No. PCT/KR2021/0130334; dated May 24, 2022; 3 pages.

Notice of Allowance; KIPO; Application 10-2021-0114230; dated Dec. 11, 2021 (submitted with original document and full text English translation).

Calvaresi, Emilia C. et al. Glucose conjugation for the specific targeting and treatment of cancer; Chem Sci, 2013, 4, 2319; Apr. 8, 2013; pp. 2319-2333.

Delatour, P. et al.; Propriétés embryotoxiques et antimitotiques en série benzimidazole; (cited with original document and translation of citation from Google Scholar™); Therapie, 1976, 31; pp. 505-515.

Notice of Reason for Refusal; Japanese Patent Application No. 2021-199359; dated Jan. 17, 2023; 9 pages; (submitted with original document and full text English translation).

Examination Report; Intellectual Property India; Application No. 202144056845; dated Mar. 28, 2023; 4 pages.

Rodrigo Aguayo-Ortiz et al., "Structured-Based Approaches for the Design of Benzimidazole-2-Carbamate Derivates as Tublin Polymerization Inhibitors", Research Article: Facultad de Quamica Departamento Mexico de Farmacia Universidad Nacional Autonoma de Mexico, Mexico. Received Oct. 11, 2016, 19 pages.

Nilambra Dogra et al., "Fenbendazole Acts as a Moderate Microtubule Destabilizing Agent and Causes Cancer Cell Death by Modulating Cellular Pathways", Scientific Reports: 2018, 8:11926: Published Online Aug. 9, 2018. www.nature.com/scientificreports, 15 pages.

Chu et al., "Potential Inhibition of Tublin Polymerisation and Proliferation of Paclitaxel-Resistant 1A9PTX22 Human Ovarian Cancer Cells by Albendazole", Anticancer Research, 29: 3791-3796, (2009).

Quan et al., "Clucose-Modification of Cisplain to Facilitate Cellular Uptake, Mitigate Toxicity to Normal Cells, and Improve Anti-Cancer Effect in Cancer Cells", Journal of Molecular Structure (2019), doi: https://doi.org/10.1016/j.molstruc.2019.127361.

Zhang et al., "Anthelmintic Drug Albandazole Arrests Human Gastric Cancer Cells at the Mitotic Phase and Induces Apoptosis", Experimental and Therapeutic Medicine 13: 595-603, 2017.

Ristanovic et al., "Impossibility of the Treatment of Inoperable Liver Multicyctic Echinococcosis Due to Adverse Reactions to Antihelminitics", Reseachgate: Article in Vojnosanitetski pregled. Military-Medical and Pharmaceutical Review—Oct. 2009.

Sung-Tae Hong, "Albendazole and Praziquantel: Review and Safety Monitoring in Korea", Infection and Chemotherapy: 2018; 50(1): 1-10, https://doi.org/10.3947/ic.2018.50.1.1.

Thaker et al., "Viral Hijacking of Cellular Metabolism", BMC Biology (2019) 17:59, https://doi.org/10.1.186/s12915-019-0678-9.

Fontaine et al., "Dengue Virus Induces and Requires Glycolysis for Optimal Replication", Journal of Virology, Feb. 2015, vol. 89. No. 4. 9 pages.

Kohio et al., "Glycolytic Control of Vacuolar-Type ATPase Activity: A Mechanism to Regulate Influenza Viral Infection", Virology (2013), http://dx.doi.org/10.1016/j.virol.2013.06.026.

Noch et al., "Oncogenic Viruses and Tumor Glucose Metabolism: Like Kids in a Candy Store", Mol. Cancer Ther. Jan. 2012: 11(1): 14-23 doi: 10.1158/1535-7163 MCT-11-0517. 16 pages.

Gokhale et al., "Glycosylation of Aromatic Amines I: Characterization of Reaction Products and Kinctic Scheme", AAPS PharSciTech, vol. 10, No. 2, Jun. 2009, DOI: 10.1208/s112249-009-9209-2, 12 pages.

Loiodice et al., "Quantifying Tubulin Concentration and Microtubule No. Throughout the Fission Yeast Cell Cycle", Biomolecules 2019, 9, 86: doi: 10.3390/biom9030086, www.mdpi.com/journal/biomolecules. 14 pages.

Chai et al., Albendazole and Mebendazole as Anti-Parasitic and Anti-Cancer Agents: an Update, Korean J. Parasitol, vol. 59, No. 3, pp. 189-225, https://doi.org/10.3347/kjp.2021.59.3.189, dated Jun. 2021.

Office Action for Chinese Application No. 202111488365.X, Dated Dec. 27, 2023 (submitted with copy of original document and full text translation).

\* cited by examiner

| Structure | Product name |
|---|---|
| 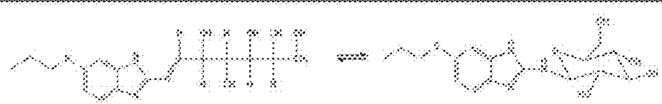 | 6-(propylthio)-1H-benzoimidazol-2-aminoglucose |
| 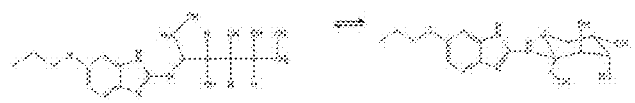 | 6-(propylthio)-1H-benzoimidazol-2-aminofructose |
| 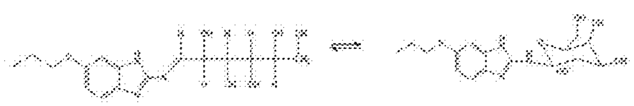 | 6-(propylthio)-1H-benzoimidazol-2-aminogalactose |
| 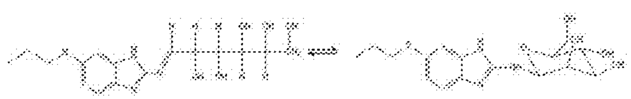 | 6-(propylthio)-1H-benzoimidazol-2-aminomannose |

FIG. 14

| Structure | Product name |
|---|---|
| 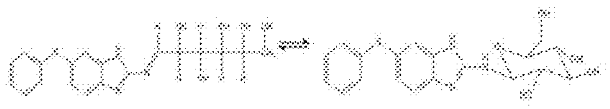 | 6-(phenylthio)-1H-benzoimidazol-2-aminoglucose |
| 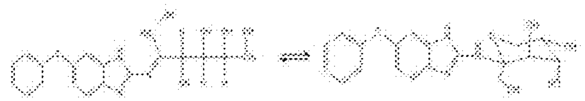 | 6-(phenylthio)-1H-benzoimidazol-2-aminofructose |
| 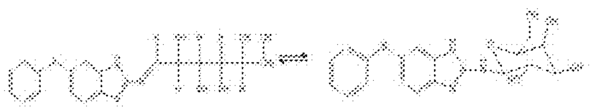 | 6-(phenylthio)-1H-benzoimidazol-2-aminogalactose |
| 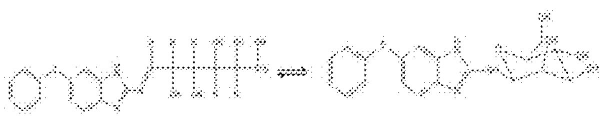 | 6-(phenylthio)-1H-benzoimidazol-2-aminomannose |

FIG. 15

| Structure | Product name |
|---|---|
| 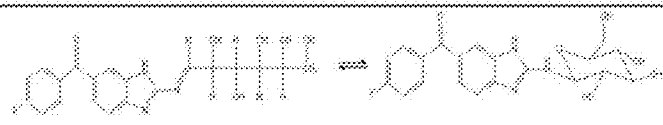 | 6-(4-fluorobenzoyl)-1H-benzimidazol-2-aminoglucose |
| 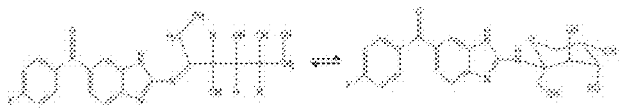 | 6-(4-fluorobenzoyl)-1H-benzimidazol-2-aminofructose |
| 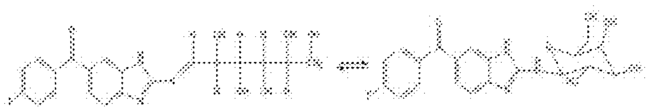 | 6-(4-fluorobenzoyl)-1H-benzimidazol-2-aminogalactose |
| 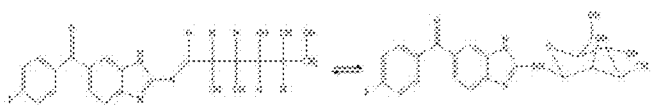 | 6-(4-fluorobenzoyl)-1H-benzimidazol-2-aminomannose |

FIG. 16

| Structure | Product name |
|---|---|
| 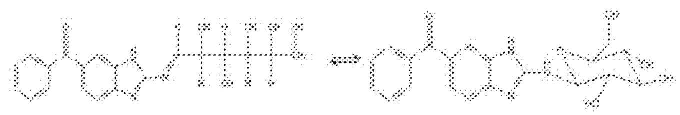 | 6-benzoyl-1H-benzimidazol-2-aminoglucose |
| 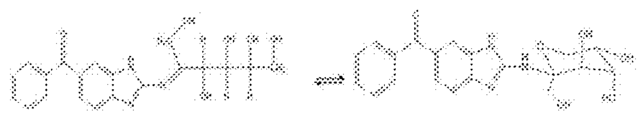 | 6-benzoyl-1H-benzimidazol-2-aminofructose |
| 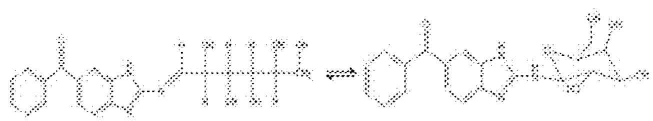 | 6-benzoyl-1H-benzimidazol-2-aminogalactose |
| 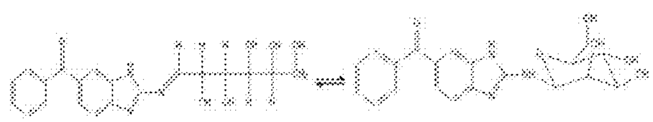 | 6-benzoyl-1H-benzimidazol-2-aminomannose |

FIG. 17

| Structure | NMR Spectrum |
|---|---|
| | 1H NMR (400 MHz, DMSO-d6): δ = 11.62 (s, 1H), 7.15 (s, 1H), 7.06 (d, J = 7.49Hz, 1H), 6.94 (d, J = 7.50Hz, 1H), 6.80 (s, 1H), 5.04 (d, J = 7.2 Hz, 1H), 3.99–3.90 (m, 1H), 3.80–3.71 (m, 1H), 3.62–3.32 (m, 4H), 2.58 (t, J = 7.14, 4.48Hz, 2H), 1.54 (m, 2H), 0.95 (t, J = 7.96Hz, 3H). |
| | 1H NMR (400 MHz, DMSO-d6): δ = 11.62 (s, 1H), 7.15 (s, 1H), 7.06 (d, J = 7.49Hz, 1H), 6.94 (d, J = 7.50Hz, 1H), 6.80 (s, 1H), 5.24 (d, 1H), 5.06 (t, 1H) 3.82–3.94 (s, 2H), 3.99–3.91 (m, 1H), 3.80–3.74 (m, 1H), 3.62–3.33 (m, 4H), 2.57 (t, J = 7.14, 4.48Hz, 2H), 1.53 (m, 2H), 0.94 (t, J = 7.96Hz, 3H). |
| | 1H NMR (400 MHz, DMSO-d6): δ = 11.62 (s, 1H), 7.15 (s, 1H), 7.06 (d, J = 7.49Hz, 1H), 6.94 (d, J = 7.50Hz, 1H), 6.80 (s, 1H), 5.04 (d, J = 7.2 Hz, 1H), 3.99–3.90 (m, 1H), 3.80–3.71 (m, 1H), 3.62–3.32 (m, 4H), 2.58 (t, J = 7.14, 4.48Hz, 2H), 1.54 (m, 2H), 0.95 (t, J = 7.96Hz, 3H). |
| | 1H NMR (400 MHz, DMSO-d6): δ = 11.62 (s, 1H), 7.15 (s, 1H), 7.06 (d, J = 7.49Hz, 1H), 6.94 (d, J = 7.50Hz, 1H), 6.80 (s, 1H), 5.04 (d, J = 7.2 Hz, 1H), 3.99–3.90 (m, 1H), 3.80–3.71 (m, 1H), 3.62–3.32 (m, 4H), 2.58 (t, J = 7.14, 4.48Hz, 2H), 1.54 (m, 2H), 0.95 (t, J = 7.96Hz, 3H). |

FIG. 18

| Structure | NMR Spectrum |
|---|---|
|  | 1H NMR (400 MHz, DMSO-d6): δ = 12.1 (s, 1H), 11.0 (s, 1H), 7.23~7.02 (m, J = Hz, 8H) 5.04 (d, J = 7.2 Hz, 1H), 3.99–3.90 (m, 1H), , 3.80–3.71 (m, 1H), 3.62–3.32 (m, 4H) |
|  | 1H NMR (400 MHz, DMSO-d6): δ = 12.1 (s, 1H), 11.0 (s, 1H), 7.23~7.02 (m, J = Hz, 8H) 5.04 (d, J = 7.2 Hz, 1H), 3.88–3.92 (s, 2H), 3.99–3.90 (m, 1H), , 3.80–3.71 (m, 1H), 3.62–3.32 (m, 4H) |
|  | 1H NMR (400 MHz, DMSO-d6): δ = 12.1 (s, 1H), 11.0 (s, 1H), 7.23~7.02 (m, J = Hz, 8H) 5.04 (d, J = 7.2 Hz, 1H), 3.25–3.33 and 3.54–3.62 (m, 2H), 3.70–4.15(m, 4H) |
|  | 1H NMR (400 MHz, DMSO-d6): δ = 12.1 (s, 1H), 11.0 (s, 1H), 7.23~7.02 (m, J = Hz, 8H) 5.04 (d, J = 7.2 Hz, 1H), 3.25–3.33 and 3.54–3.62 (m, 2H), 3.70–4.15(m, 4H) |

FIG. 19

| Structure | NMR Spectrum |
|---|---|
| | 1H NMR (400 MHz, DMSO-d6): δ = 12.1 (s, 1H), 11.0 (s, 1H), 7.42~7.12 (m, J = Hz, 7H), 5.04 (d, J = 7.2 Hz, 1H), 3.99–3.90 (m, 1H), , 3.80–3.71 (m, 1H), 3.62–3.32 (m, 4H) |
| | 1H NMR (400 MHz, DMSO-d6): δ = 12.1 (s, 1H), 11.0 (s, 1H), 7.42~7.12 (m, J = Hz, 7H), 5.04 (d, J = 7.2 Hz, 1H), 3.88–3.92 (s, 2H), 3.99–3.90 (m, 1H), , 3.80–3.71 (m, 1H), 3.62–3.32 (m, 4H) |
| | 1H NMR (400 MHz, DMSO-d6): δ = 12.1 (s, 1H), 11.0 (s, 1H), 7.42~7.12 (m, J = Hz, 7H), 5.04 (d, J = 7.2 Hz, 1H), 3.25–3.33 (s, 2H), 3.54–3.62 (m, 2H) 3.70–4.15(m, 4H) |
| | 1H NMR (400 MHz, DMSO-d6): δ = 12.1 (s, 1H), 11.0 (s, 1H), 7.42~7.12 (m, J = Hz, 7H), 5.04 (d, J = 7.2 Hz, 1H), 3.25–3.33 (m, 2H), 3.54–3.62 (m, 2H) and 3.70–4.15(m, 4H) |

FIG. 20

| Structure | NMR Spectrum |
|---|---|
| | 1H NMR (400 MHz, DMSO-d6): δ = 12.1 (s, 1H), 11.0 (s, 1H), 7.44~7.20 (m, J = Hz, 8H), 5.04 (d, J = 7.2 Hz, 1H), 3.99–3.90 (m, 1H), 3.80–3.71 (m, 1H), 3.62–3.32 (m, 4H) |
| | 1H NMR (400 MHz, DMSO-d6): δ = 12.1 (s, 1H), 11.0 (s, 1H), 7.44~7.20 (m, J = Hz, 8H), 5.04 (d, J = 7.2 Hz, 1H), 3.88-3.92 (s, 2H), 3.99–3.90 (m, 1H), 3.80–3.71 (m, 1H), 3.62–3.32 (m, 4H) |
| | 1H NMR (400 MHz, DMSO-d6): δ = 12.1 (s, 1H), 11.0 (s, 1H), 7.44~7.20 (m, J = Hz, 8H), 5.04 (d, J = 7.2 Hz, 1H), 3.25–3.33 (m, 1H), 3.54–3.62 (m, 2H), 3.70–4.15(m, 4H) |
| | 1H NMR (400 MHz, DMSO-d6): δ = 12.1 (s, 1H), 11.0 (s, 1H), 7.44~7.20 (m, J = Hz, 8H), 5.04 (d, J = 7.2 Hz, 1H), 3.25–3.33 (m, 1H), 3.54–3.62 (m, 2H), 3.70–4.15(m, 4H) |

MICELLE COMPRISING BENZIMIDAZOLE-CARBOHYDRATE CONJUGATE COMPOUND, PREPARATION METHOD THEREOF AND USE THEREOF AS ANTICANCER AGENT OR ANTIVIRAL AGENT COMPRISING THE SAME

CROSS-REFERENCE TO RELATED APPLICATION

This application claims priority to and the benefit of Korean Patent Application No. 10-2021-0114230, filed on Aug. 27, 2021, the disclosure of which is incorporated herein by reference in its entirety.

TECHNICAL FIELD

The present disclosure relates to a micelle comprising a benzimidazole-carbohydrate conjugate compound, a preparation method thereof, and use thereof as an anticancer agent or an antiviral agent comprising the same.

BACKGROUND

Benzimidazole is a compound in which an imidazole ring is attached to a benzene ring, and attracts attention as a precursor since Benzimidazole shows a variety of bioactivities and physiological activities. According to studies, compounds having the above benzimidazole structure affect various types of diseases. For example, antiinflammatory analgesic, antifungal, anticancer, anthelmintic, antihistamine and the like, which contain the compounds having the above benzimidazole structure, have been developed.

According to papers, benzimidazole can come into cells through cell membranes and suppress formation of microtubules (see *Chem Biol Drug Des.*, 2017 July; 90(1):40-51; *Scientific REPORTS*, 2018, 8:11926; and *ANTICANCER RESEARCH*, 29: 3791-3796, 2009). However, benzimidazole comes into normal cells as well as abnormal cells (e.g., cancer expressed cells and virally infected cells). Accordingly, benzimidazole suppresses formation of microtubules in both the normal cells and the abnormal cells, adversely affecting the normal cells (see Vojnosanit Pregl. 2008 July; 65(7):539-44, Infect Chemother 2018; 50(1):1-10).

Additionally, the cancer cells, the virally infected cells and the like absorb large amounts of glucose. The cancer cells and the virally infected cells use microtubules to move glucose transporter (GLUT) channels to the cell membranes necessarily, and in particular, the cancer cells are known to generate 1,000 times more GLUT channels than the normal cells (see L. Quan et al./*Journal of Molecular Structure* 1203 (2020) 127361).

When benzimidazole derivatives are intensively absorbed into the cancer cells or the virally infected cells rather than the normal cells, formation of the microtubules can be suppressed, generation of the GLUT channels can be suppressed, and absorption of glucose can be prevented, thereby significantly suppressing a proliferation of the cancer cells or a proliferation of viruses in the virally infected cells. Thus, the immune system in the body attacks the cancer cells or the virally infected cells, the proliferation of which is suppressed as described above, and produces anticancer and antiviral effects (see *EXPERIMENTAL AND THERAPEUTIC MEDICINE* 13: 595-603, 2017).

Albendazole and fenbendazole used as an anthelmintic drug are benzimidazole carbamate-based compounds, and when being absorbed into cells, are absorbed through cell membranes. Accordingly, albendazole and fenbendazole are absorbed into virally infected cells as well as normal cells. It is difficult for the compounds to be selectively absorbed only into cancer cells or virally infected cells.

Further, studies show that glucose as an energy source of every cell is absorbed through GLUT channels of cells and that virally infected cells consume larger amounts of glucose as an energy source than normal cells (see BMC Biology (2019) 17:59), (J Virol 89:2358-2366.), (Virology. 2013; 444 (1-2):301-9). Furthermore, the virally infected cells change energy metabolism of host cells to use larger amounts of glucose as an energy source than the normal cells, and activate the GLUT channels further than the normal cells to absorb glucose through the GLUT channels quickly and proliferate viruses (see Mol Cancer Ther. 2012 January; 11(1): 14-23).

In conclusion, cancer cells and virally infected cells absorb larger amounts of sugar compounds containing glucose than normal cells or cells that are not infected by viruses.

In this context, a new micelle prepared using a benzimidazole derivative can be designed based on the fact that cancer cells and virally infected cells absorb larger amounts of sugar compounds containing glucose than normal cells or cells that are not infected by viruses, and can be provided using a simple process without causing large costs.

PRIOR ART DOCUMENT

Patent Documents (Patent document 1) International Patent Publication No. WO1998/051304 published on Nov. 19, 1998)
(Patent document 2) International Patent Publication No. WO2005/058870 published Jun. 30, 2005)
(Patent document 3) International Patent Publication No. WO1998/056761 published Dec. 17, 1998)

SUMMARY

Technical Problems

To solve the above problems, the present disclosure is directed to a micelle comprising a benzimidazole-carbohydrate conjugate compound, a preparation method thereof, and use thereof as an anticancer agent or an antiviral agent comprising the same.

Aspects according to the present disclosure are not limited to the above ones, and other aspects and advantages that are not mentioned above can be clearly understood by one skilled in the art from the following description.

Technical Solutions

The present disclosure is to provide a micelle comprising a benzimidazole-carbohydrate conjugate compound represented by the following chemical formula 1:

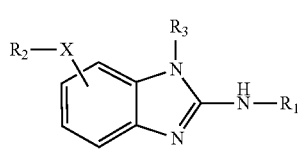

[Chemical formula 1]

Wherein, $R_1$ is a carbohydrate residue, and the carbohydrates may be selected from a tetrose aldose (e.g., erythrose and threose), a pentose aldose (e.g., ribose, arabinose, xylose and lyxose), a hexose aldose (e.g., allose, altrose, glucose, mannose, gulose, idose, galactose and talose), a tetrose ketose (e.g., erythrulose), a pentose ketose (e.g., ribulose and xylulose), a hexose ketose (e.g., psicose, fructose, sorbose and tagatose), isomers thereof, oxides thereof (an aldehyde (—CHO) is converted to a carboxy (—COOH)), deoxy derivatives thereof (a hydroxy (—OH) is converted to a hydrogen (—H); e.g., 2-deoxyribose and 2-deoxyglucose), amino sugars thereof (a hydroxy (—OH) is converted to a nitrogen hydride (—NH); e.g., N-acetylglucosamine and N-acetylgalactosamine), glycosides thereof, or disaccharides thereof, preferably, glucose, fructose, galactose, maltose or xylose, $R_2$ and $R_3$ are identical or different and are a hydrogen or a replaceable hydrocarbon group, for example, an alkyl group having 1-10 carbon atoms, and an aryl group or a heteroaryl group having 3-10 ring atoms, and the alkyl group, the aryl group and the heteroaryl group may be replaced with a substituent selected from a halogen, cyano, hydroxyl, thiol, amino, alkyl, alkoxy, alkylamino, dialkylamino, aryl, aryloxy, arylamino, diarylamino or heteroaryl group, and X may be selected from a group consisting of —O—, —S—, —SO—, —SO$_2$—, —NH—, —N($R_2$)—, —CH$_2$—, —CH($R_2$)— and —CO—.

In one embodiment, the benzimidazole-carbohydrate conjugate compound may be a compound represented by the following chemical formula 2:

[Chemical formula 2]

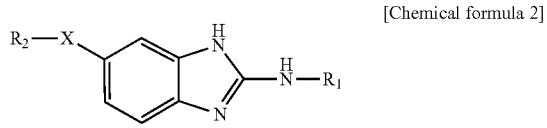

Wherein, $R_1$, $R_2$ and X are the same as those defined above.

In one embodiment, the —NH—$R_1$ moiety in chemical formula 1 or 2 above, may have one of the following structures:

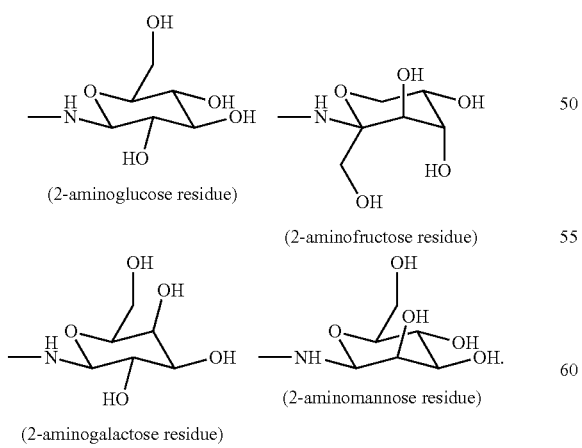

(2-aminoglucose residue)
(2-aminofructose residue)
(2-aminogalactose residue)
(2-aminomannose residue)

In one embodiment, the benzimidazole moiety in chemical formula 1 or 2 above may have one of the following structures:

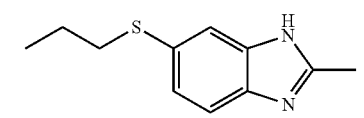

(albendazole residue without 2-carbamate)

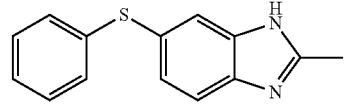

(febendazole residue without 2-carbamate)

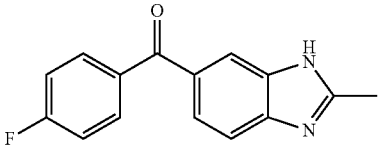

(flubendazole residue without 2-carbamate)

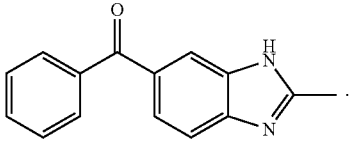

(mebendazole residue without 2-carbamate)

In one embodiment, the benzimidazole-carbohydrate conjugate compound may be selected from the following compounds:

6-(propylthio)-1H-benzoimidazol-2-aminoglucose, 6-(propylthio)-1H-benzoimidazol-2-aminofructose, 6-(propylthio)-1H-benzoimidazol-2-aminogalactose, and 6-(propylthio)-1H-benzoimidazol-2-aminomannose, as an albendazole-D-carbohydrate conjugate compound;

6-(phenylthio)-1H-benzoimidazol-2-aminoglucose, 6-(phenylthio)-1H-benzoimidazol-2-aminofructose, 6-(phenylthio)-1H-benzoimidazol-2-aminogalactose, and 6-(phenylthio)-1H-benzoimidazol-2-aminomannose, as a fenbendazole-D-carbohydrate conjugate compound;

6-(4-fluorobenzoyl)-1H-benzimidazol-2-aminoglucose, 6-(4-fluorobenzoyl)-1H-benzimidazol-2-aminofructose, 6-(4-fluorobenzoyl)-1H-benzimidazol-2-aminogalactose, and 6-(4-fluorobenzoyl)-1H-benzimidazol-2-aminomannose, as a flubendazole-D-carbohydrate conjugate compound; and 6-benzoyl-1H-benzimidazol-2-aminoglucose, 6-benzoyl-1H-benzimidazol-2-aminofructose, 6-benzoyl-1H-benzimidazol-2-aminogalactose, and 6-benzoyl-1H-benzimidazol-2-aminomannose, as a mebendazole-D-carbohydrate conjugate compound.

In one embodiment, the micelle may further comprise a benzimidazole-ammonium compound represented by the following chemical formula 1b:

[Chemical formula 1b]

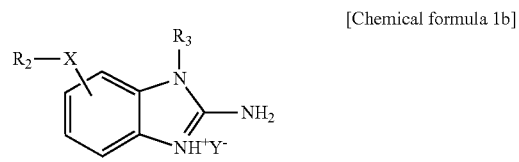

Wherein, $R_2$ and $R_3$ are identical or different and are a hydrogen or a replaceable hydrocarbon group, for example, an alkyl group having 1-10 carbon atoms, and an aryl group or a heteroaryl group having 3-10 ring atoms, and the alkyl group, the aryl group and the heteroaryl group may be replaced with a substituent selected from a halogen, cyano, hydroxyl, thiol, amino, alkyl, alkoxy, alkylamino, dialkylamino, aryl, aryloxy, arylamino, diarylamino or heteroaryl group, X may be selected from a group consisting of —O—, —S—, —SO—, —SO$_2$—, —NH—, —N(R$_2$)—, —CH$_2$—, —CH(R$_2$)— and —CO—, and $Y^-$ is a conjugate base of acid ($H^+$) and may be selected from $Cl^-$, $Br^-$, $I^-$, $F^-$, $NO_3^-$, $CH_3COO^-$, $HCOO^-$, $HCO_3^-$, $CO_3^{2-}$, $H_2PO_4^-$, $HPO_4^{2-}$, $HSO_4^-$, $SO_4^{2-}$, or $ClO_4^-$.

In one embodiment, the benzimidazole-ammonium compound may be selected from a compound represented by the following chemical formula 2b:

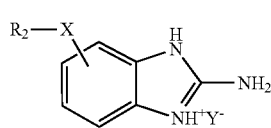

[Chemical formula 2b]

Wherein, $R_2$, X and $Y^-$ are the same as those defined above.

In one embodiment, a molar ratio of the benzimidazole-ammonium compound to the benzimidazole-carbohydrate conjugate compound may be 1:500-500:1.

In one embodiment, concentrations of a benzimidazole-ammonium derivative and the benzimidazole-carbohydrate conjugate compound left in cells, into which the micelle is inserted, for 24 to 72 hours may be kept higher than concentrations of the benzimidazole-ammonium derivative and the benzimidazole-carbohydrate conjugate compound discharged from the cells into which the micelle is inserted, after the micelle is inserted into the cells.

To achieve the above objectives, the present disclosure is to provide a preparation method of a micelle, which may comprise mixing a benzimidazole-carbohydrate conjugate compound represented by the following chemical formula 1 with a benzimidazole-ammonium compound represented by the following chemical formula 1b:

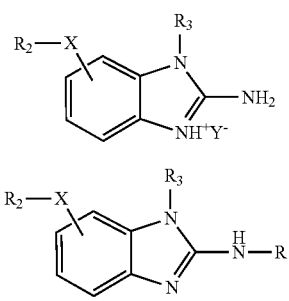

[Chemical formula 1b]

[Chemical formula 1]

Wherein, $R_1$ is a carbohydrate residue, and the carbohydrates are selected from a tetrose aldose (e.g., erythrose and threose), a pentose aldose (e.g., ribose, arabinose, xylose and lyxose), a hexose aldose (e.g., allose, altrose, glucose, mannose, gulose, idose, galactose and talose), a tetrose ketose (e.g., erythrulose), a pentose ketose (e.g., ribulose and xylulose), a hexose ketose (e.g., psicose, fructose, sorbose and tagatose), isomers thereof, oxides thereof (an aldehyde (—CHO) is converted to a carboxy (—COOH)), deoxy derivatives thereof (a hydroxy (—OH) is converted to a hydrogen (—H); e.g., 2-deoxyribose and 2-deoxyglucose), amino sugars thereof (a hydroxy (—OH) is converted to a nitrogen hydride (—NH); e.g., N-acetylglucosamine and N-acetylgalactosamine), glycosides thereof, or disaccharides thereof, preferably, glucose, fructose, galactose, maltose or xylose, $R_2$ and $R_3$ are identical or different and are a hydrogen or a replaceable hydrocarbon group, for example, an alkyl group having 1-10 carbon atoms, and an aryl group or a heteroaryl group having 3-10 ring atoms, and the alkyl group, the aryl group and the heteroaryl group may replaced with a substituent selected from a halogen, cyano, hydroxyl, thiol, amino, alkyl, alkoxy, alkylamino, dialkylamino, aryl, aryloxy, arylamino, diarylamino or heteroaryl group, X may be selected from a group consisting of —O—, —S—, —SO—, —SO$_2$—, —NH—, —N(R$_2$)—, —CH$_2$—, —CH(R$_2$)— and —CO—, and $Y^-$ is a conjugate base of acid ($H^+$) and may be selected from $Cl^-$, $Br^-$, $I^-$, $F^-$, $NO_3^-$, $CH_3COO^-$, $HCOO^-$, $HCO_3^-$, $CO_3^{2-}$, $H_2PO_4^-$, $HPO_4^{2-}$, $HSO_4^-$, $SO_4^{2-}$, or $ClO_4$.

In one embodiment, the preparation method of a micelle may comprise mixing a benzimidazole-carbohydrate conjugate compound represented by the following chemical formula 2 with a benzimidazole-ammonium compound represented by the following chemical formula 2b:

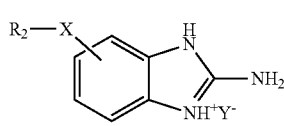

[Chemical formula 2b]

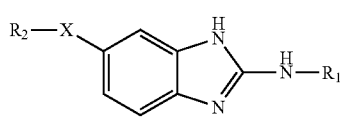

[Chemical formula 2]

Wherein, $R_1$, $R_2$, X and $Y^-$ are the same as those defined above.

In one embodiment, the benzimidazole-ammonium compound represented by the chemical formula 1b or 2b above may be prepared as a result of reaction of a 2-aminobenzimidazole compound of the following chemical formula 1a or 2a with acids:

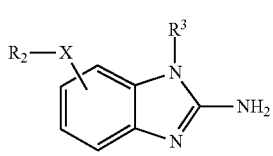

[Chemical formula 1a]

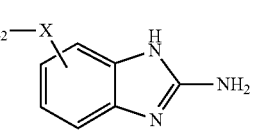

[Chemical formula 2a]

Wherein, $R_2$, $R_3$ and X are the same as those defined above.

In one embodiment, the benzimidazole-carbohydrate conjugate compound represented by the chemical formula 1 or 2 above may be obtained as a result of reaction of a carbohydrate with the 2-aminobenzimidazole compound of the following chemical formula 1a or 2a, to form an imine bond:

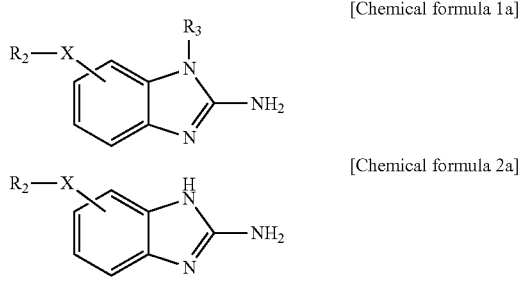

[Chemical formula 1a]

[Chemical formula 2a]

Wherein, $R_2$, $R_3$ and X are the same as those defined above.

In one embodiment, a substituent enabling an imine reaction, in the 2-aminobenzimidazole compound of chemical formula 1a or 2a, may be protected or shielded in advance.

To achieve the above objectives, the present disclosure is to provide a pharmaceutical composition containing the micelle comprising the benzimidazole-carbohydrate conjugate compound of chemical formula 1 or 2 above.

In one embodiment, the pharmaceutical composition may suppresses formation of microtubules, and suppress absorption of carbohydrates, preferably, sugars compounds comprising glucose.

In one embodiment, the pharmaceutical composition may show anticancer or antiviral activity.

In one embodiment, the pharmaceutical composition may be absorbed through GLUT channels.

Advantageous Effects

According to the present disclosure, a micelle comprising a benzimidazole-ammonium compound and a benzimidazole-carbohydrate conjugate compound shows anticancer or antiviral activity.

It is to be understood that advantages of the subject matter of the disclosure are not limited to the above advantages, and construed as including all advantages inferred from configurations in the appended claims.

BRIEF DESCRIPTION OF DRAWINGS

The accompanying drawings constitute a part of the specification, illustrate one or more embodiments in the disclosure, and together with the specification, explain the disclosure, wherein:

FIG. 1 is a schematic view showing that a micelle comprising an albendazole-ammonium (Al—$NH_3^+$) compound and an albendazole-glucose (Al-G) compound in one embodiment comes into a cell through a GLUT channel;

FIG. 13 is a view showing structural formulas and names of an albendazole-D-carbohydrate conjugate;

FIG. 14 is a view showing structural formulas and names of a fenbendazole-D-carbohydrate conjugate;

FIG. 15 is a view showing structural formulas and names of a flubendazole-D-carbohydrate conjugate;

FIG. 16 is a view showing structural formulas and names of a mebendazole-D-carbohydrate conjugate;

FIG. 17 is a view showing an NMR spectrum of an albendazole-D-carbohydrate conjugate;

FIG. 18 is a view showing an NMR spectrum of a fenbendazole-D-carbohydrate conjugate;

FIG. 19 is a view showing an NMR spectrum of a flubendazole-D-carbohydrate conjugate; and FIG. 20 is a view showing an NMR spectrum of a mebendazole-D-carbohydrate conjugate.

DETAILED DESCRIPTION

Figure 2:
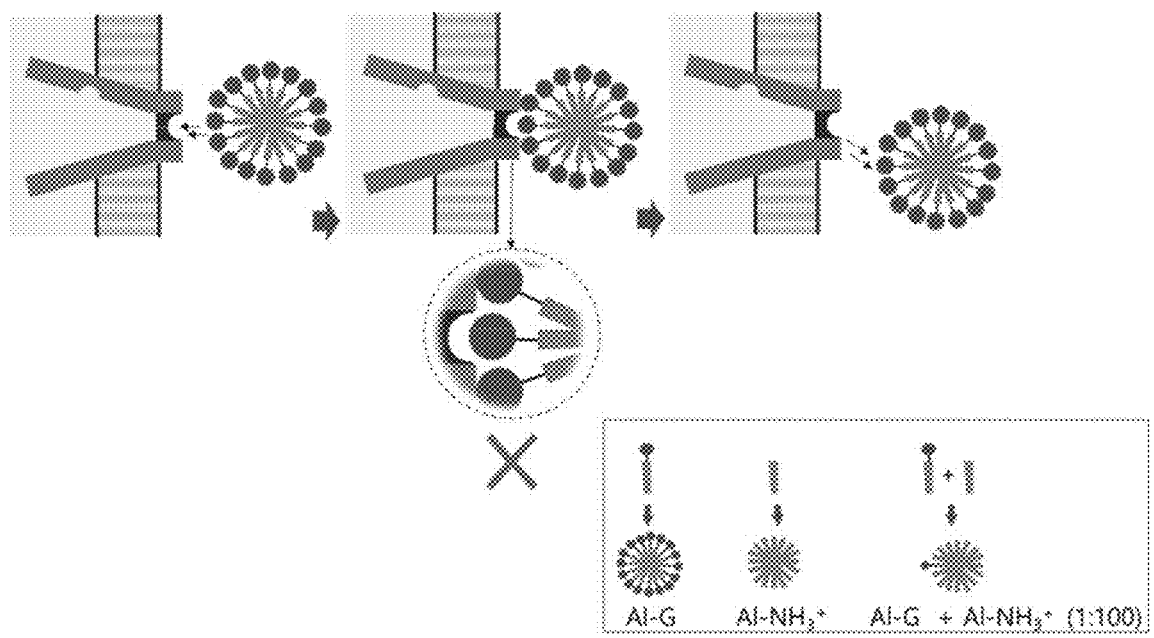
FIG. 2 is a schematic view showing that a GLUT channel is not easily open to a micelle comprising an albendazole-glucose (Al-G) compound in one embodiment, causing difficulty in entry of the micelle to the GLUT channel.

All the terms and words used herein should not be limitedly interpreted as those defined commonly or those defined in dictionaries, and can be properly defined and used by the applicant of the disclosure such that the applicant describes the subject matter of the disclosure in the best possible way. Furthermore, it is to be understood that the terms and the words are interpreted as meanings and concepts consistent with their meanings and concepts within the technical spirit of the disclosure.

The terms used in the disclosure are used only to describe preferred embodiments, and not intended to limit details of the subject matter of the disclosure. It is to be understood that the terms are defined considering a variety of possibilities of the subject matter of the disclosure.

Throughout the disclosure, the singular forms "a", "an" and "the" can be construed as including the plural forms as well, unless explicitly indicated otherwise, and similarly, the plural forms can be construed as including the singular forms as well.

Throughout the disclosure, when one component "comprises" or "includes" another component, it does not mean excluding an additional component but mean including an additional component, unless stated to the contrary.

In the disclosure, detailed descriptions of known technologies including conventional technologies in relation to the disclosure are omitted if they are deemed to make the gist of the disclosure unnecessarily vague.

For an understanding of the subject matter of the disclosure, the terms used herein are briefly defined as follows. However, the terms and the definitions of the terms are not intended to limit the subject matter of the disclosure.

The term "anticancer agent" denotes a substance or a drug that suppresses growth or a proliferation of cancer cells.

The term "antiviral" denotes suppression of a proliferation of virally infected cells, and the term "antiviral agent" denotes a substance or a drug that suppresses a proliferation of virally infected cells.

The term "carbohydrate" is used to totally refer to organic compounds comprised of sugar.

The term "inhibition of absorption of sugar compounds" denotes inhibiting sugar compounds from being absorbed or coming into cells.

The term "tubulin" denotes proteins constituting microtubules present in almost all cells of living things.

The term "microtubule" denotes a tube which is comprised of a polymer of proteins called tubulin, which constitutes a cytoskeleton, and through which substances in cells move.

The term "cell division" denotes a division of a single mother cell of a living thing into two cells after a nuclear division and cytokinesis.

The term "micelle" is a product of a voluntary gathering of amphipathic molecules, exhibiting hydrophilicity and lipophilicity at the same time, in an aqueous solution. A hydrophilic moiety forms an outer surface of the micelle, and is exposed to water, while a lipophilic moiety is inside the micelle and protected from water.

Hereafter, the subject matter of the present disclosure is described.

(1) Micelle Comprising Benzimidazole-Carbohydrate Conjugate Compound

The first objective of the present disclosure is to provide a micelle comprising a benzimidazole-carbohydrate conjugate compound represented by the following chemical formula 1.

[Chemical formula 1]

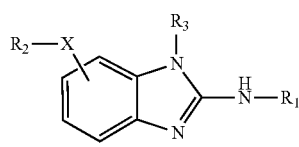

Wherein, $R_1$ is a carbohydrate residue, and the carbohydrates may be selected from a tetrose aldose (e.g., erythrose and threose), a pentose aldose (e.g., ribose, arabinose, xylose and lyxose), a hexose aldose (e.g., allose, altrose, glucose, mannose, gulose, idose, galactose and talose), a tetrose ketose (e.g., erythrulose), a pentose ketose (e.g., ribulose and xylulose), a hexose ketose (e.g., psicose, fructose, sorbose and tagatose), isomers thereof, oxides thereof (an aldehyde (—CHO) is converted to a carboxy (—COOH)), deoxy derivatives thereof (a hydroxy (—OH) is converted to a hydrogen (—H); e.g., 2-deoxyribose and 2-deoxyglucose), amino sugars thereof (a hydroxy (—OH) is converted to a nitrogen hydride (—NH); e.g., N-acetylglucosamine and N-acetylgalactosamine), glycosides thereof, or disaccharides thereof, preferably, glucose, fructose, galactose, maltose or xylose, $R_2$ and $R_3$ are identical or different and are be a hydrogen or a replaceable hydrocarbon group, for example, an alkyl group having 1-10 carbon atoms, and an aryl group or a heteroaryl group having 3-10 ring atoms. The alkyl group, the aryl group and the heteroaryl group may be replaced with a substituent selected from a halogen, cyano, hydroxyl, thiol, amino, alkyl, alkoxy, alkylamino, dialkylamino, aryl, aryloxy, arylamino, diarylamino or heteroaryl group, and X may be selected from a group consisting of —O—, —S—, —SO—, —SO$_2$—, —NH—, —N($R_2$)—, —CH$_2$—, —CH($R_2$)— and —CO—.

The compound in chemical formula 1 may be understood in a form in which a carbohydrate residue bonds to a 2-amino group of a 2-aminobenzimidazole structure or a form in which an aminated carbohydrate bonds to a 2-position of a benzimidazole structure.

In one embodiment, the benzimidazole-carbohydrate conjugate compound may be a compound represented by the following chemical formula 2.

[Chemical formula 2]

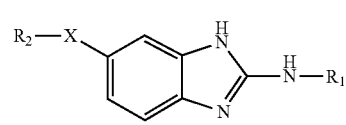

Wherein, $R_1$, $R_2$ and X are the same as those defined above.

In the above chemical formula 1 or 2 of one embodiment, the —NH—$R_1$ moiety may have one of the following structures:

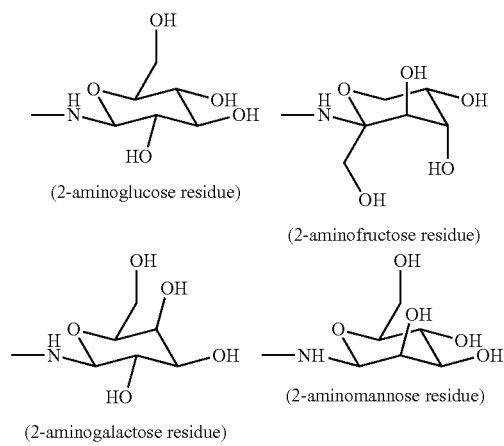

(2-aminoglucose residue)
(2-aminofructose residue)
(2-aminogalactose residue)
(2-aminomannose residue)

In the above chemical formula 1 or 2 of one embodiment, the benzimidazole moiety may have one of the following structures:

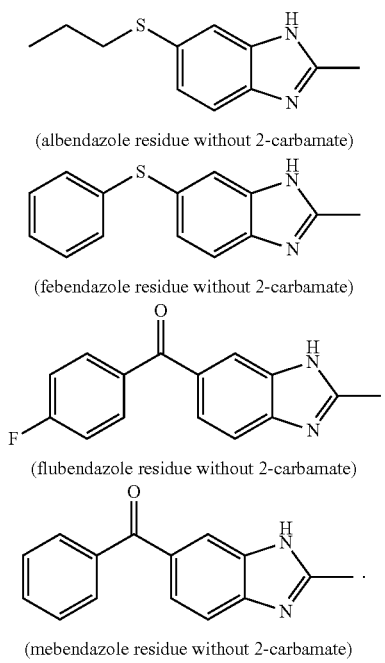

(albendazole residue without 2-carbamate)

(febendazole residue without 2-carbamate)

(flubendazole residue without 2-carbamate)

(mebendazole residue without 2-carbamate)

In one embodiment, the benzimidazole-carbohydrate conjugate compound may be selected from the following compounds:

6-(propylthio)-1H-benzoimidazol-2-aminoglucose, 6-(propylthio)-1H-benzoimidazol-2-aminofructose, 6-(propylthio)-1H-benzoimidazol-2-aminogalactose, and 6-(propylthio)-1H-benzoimidazol-2-aminomannose, as an albendazole-D-carbohydrate conjugate compound;

6-(phenylthio)-1H-benzoimidazol-2-aminoglucose, 6-(phenylthio)-1H-benzoimidazol-2-aminofructose, 6-(phenylthio)-1H-benzoimidazol-2-aminogalactose, and 6-(phenylthio)-1H-benzoimidazol-2-aminomannose, as a fenbendazole-D-carbohydrate conjugate compound;

6-(4-fluorobenzoyl)-1H-benzimidazol-2-aminoglucose, 6-(4-fluorobenzoyl)-1H-benzimidazol-2-aminofructose, 6-(4-fluorobenzoyl)-1H-benzimidazol-2-aminogalactose, and 6-(4-fluorobenzoyl)-1H-benzimidazol-2-aminomannose, as a flubendazole-D-carbohydrate conjugate compound; and 6-benzoyl-1H-benzimidazol-2-aminoglucose, 6-benzoyl-1H-benzimidazol-2-aminofructose, 6-benzoyl-1H-benzimidazol-2-aminogalactose, and 6-benzoyl-1H-benzimidazol-2-aminomannose, as a mebendazole-D-carbohydrate conjugate compound.

In the benzimidazole-carbohydrate conjugate compound included in the micelle, according to the disclosure, the carbohydrate moiety may have both of the linear and cyclic forms. It can be said that the linear form is more reliable than the cyclic form in pentoses and hexoses thermodynamically. However, since the linear form and the cyclic form are in equilibrium, in a solution, the overall pharmacological effect makes no difference even if any one of the linear form and the cyclic form shows efficacy.

In one embodiment, the micelle may further comprise a benzimidazole-ammonium compound represented by the following chemical formula 1b.

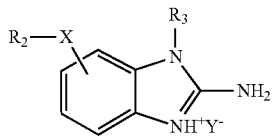

[Chemical formula 1b]

Wherein, $R_2$ and $R_3$ are identical or different and are a hydrogen or a replaceable hydrocarbon group, for example, an alkyl group having 1-10 carbon atoms, and an aryl group or a heteroaryl group having 3-10 ring atoms. The alkyl group, the aryl group and the heteroaryl group may be replaced with a substituent selected from a halogen, cyano, hydroxyl, thiol, amino, alkyl, alkoxy, alkylamino, dialkylamino, aryl, aryloxy, arylamino, diarylamino or heteroaryl group, X may be selected from a group consisting of —O—, —S—, —SO—, —SO$_2$—, —NH—, —N(R$_2$)—, —CH$_2$—, —CH(R$_2$)— and —CO—, and $Y^-$ is a conjugate base of acid ($H^+$) and may be selected from $Cl^-$, $Br^-$, $I^-$, $F^-$, $NO_3^-$, $CH_3COO^-$, $HCOO^-$, $HCO_3^-$, $CO_3^{2-}$, $H_2PO_4^-$, $HPO_4^{2-}$, $HSO_4^-$, $SO_4^{2-}$, or $ClO_4^-$.

In one embodiment, the benzimidazole-ammonium compound may be a compound represented by the following chemical formula 2b.

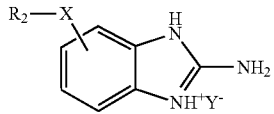

[Chemical formula 2b]

Wherein, $R_2$, X and $Y^-$ are the same as those defined above.

In one embodiment, a molar ratio of the benzimidazole-ammonium compound to the benzimidazole-carbohydrate conjugate compound may be 500:1-1:500, preferably, 500:1-1:1, 200:1-1:1, 200:1-10:1, 100:1-1:1 or 100:1-5:1.

Figure 1:
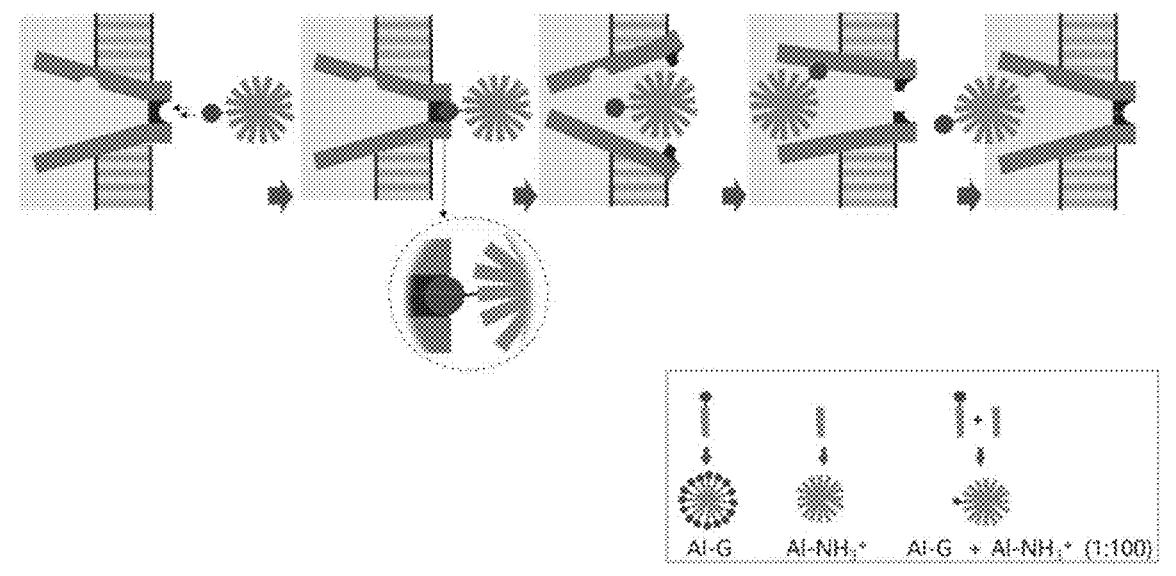
Figure 3:
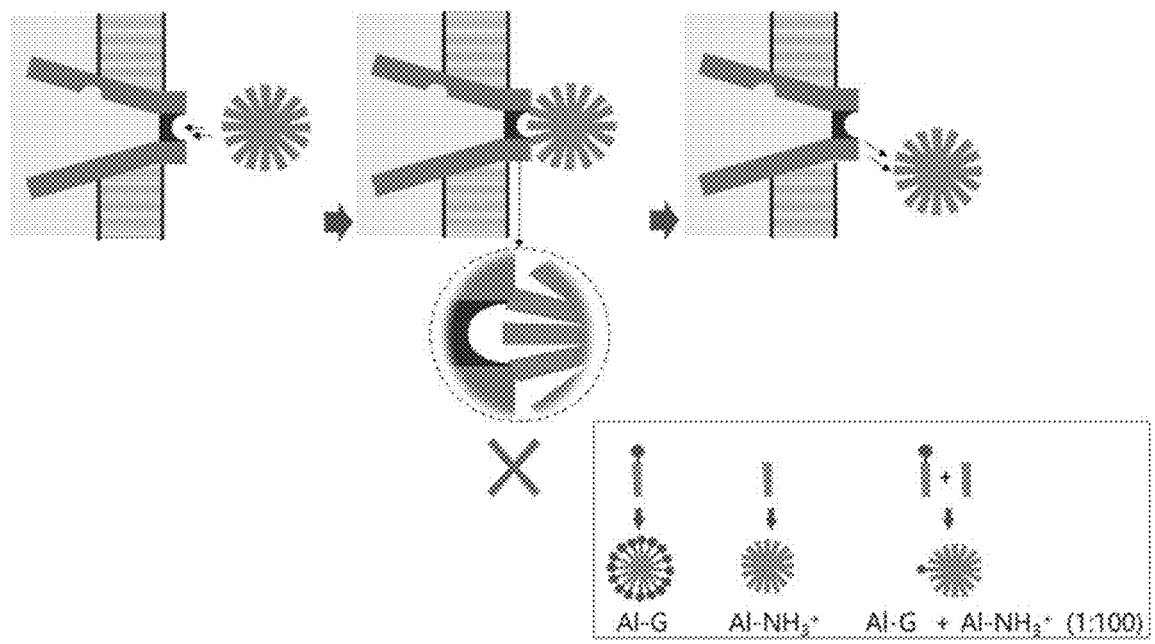
FIG. 3 is a schematic view showing that a GLUT channel is not easily open to a micelle comprising an albendazole-ammonium (Al—$NH_3^+$) compound in one embodiment, causing difficulty in entry of the micelle to the GLUT channel.

FIG. 1 shows a micelle comprising a benzimidazole-ammonium compound and a benzimidazole-carbohydrate conjugate compound, FIG. 2 is a micelle comprising a benzimidazole-carbohydrate conjugate single compound, and FIG. 3 shows a micelle comprising a benzimidazole-ammonium single compound.

Referring to FIGS. 4 to 11, the micelle comprising a benzimidazole-ammonium compound and a benzimidazole-carbohydrate conjugate compound (FIG. 1) shows tens to hundreds times more effective than the micelle comprising a benzimidazole-carbohydrate conjugate single compound (FIG. 2) or the micelle comprising a benzimidazole-ammonium single compound (FIG. 3).

In one embodiment, the micelle is to maintain concentrations of a benzimidazole-ammonium derivative and the benzimidazole-carbohydrate conjugate compound left in cells, into which the micelle is inserted, for 24 to 72 hours may be kept higher than concentrations of the benzimidazole-ammonium derivative and the benzimidazole-carbohydrate conjugate compound discharged from the cells into which the micelle is inserted, after the micelle is inserted into the cells.

When the benzimidazole-carbohydrate conjugate compound is absorbed into a mono substance rather than the micelle, large amounts of the benzimidazole-ammonium compound and the benzimidazole-carbohydrate conjugate compound are barely absorbed for a short period of time, thereby making it hard to ensure efficacy sufficiently.

The micelle comprising the benzimidazole-carbohydrate conjugate compound according to the disclosure is characterized in that large amounts of drugs are intensively absorbed into cancer cells and virally infected cells in which GLUT channels are activated further than those in normal cells such that efficacy of the drugs is shown within a short period of time.

(2) Preparation Method of Micelle Comprising Benzimidazole-Carbohydrate Conjugate Compound The second objective of the present disclosure is to provide a preparation method of a micelle in which a benzimidazole-carbohydrate conjugate compound represented by the following chemical formula 1 is mixed with a benzimidazole-ammonium compound represented by the following chemical formula 1b.

[Chemical formula 1b]

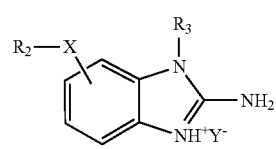

[Chemical formula 1]

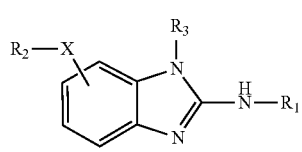

Wherein, $R_1$, $R_2$, $R_3$, X and $Y^-$ are the same as those defined above.

In one embodiment, the preparation method of a micelle may involve mixing a benzimidazole-carbohydrate conjugate compound represented by the following chemical formula 2 with a benzimidazole-ammonium compound represented by the following chemical formula 2b.

[Chemical formula 2b]

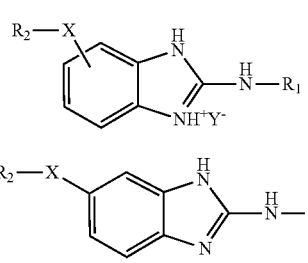

[Chemical formula 2]

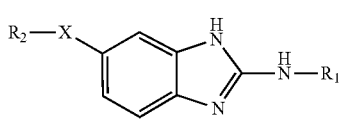

Wherein, $R_1$, $R_2$, X and $Y^-$ are the same as those defined above.

The micelle according to the present disclosure may be prepared using various methods, and hereunder, an example of the preparation method is described. Reaction formula 1 hereunder may be presented as an example of the preparation method of a micelle according to the disclosure.

Reaction formula 1 shows that a benzimidazole-ammonium compound, produced by combining a 2-aminobenzimidazole compound with hydrochloric acid (HCl), is mixed with a benzimidazole-carbohydrate conjugate compound in which a 2-aminobenzimidazole compound combines with a carbohydrate, to form a micelle.

[Reaction formula 1]

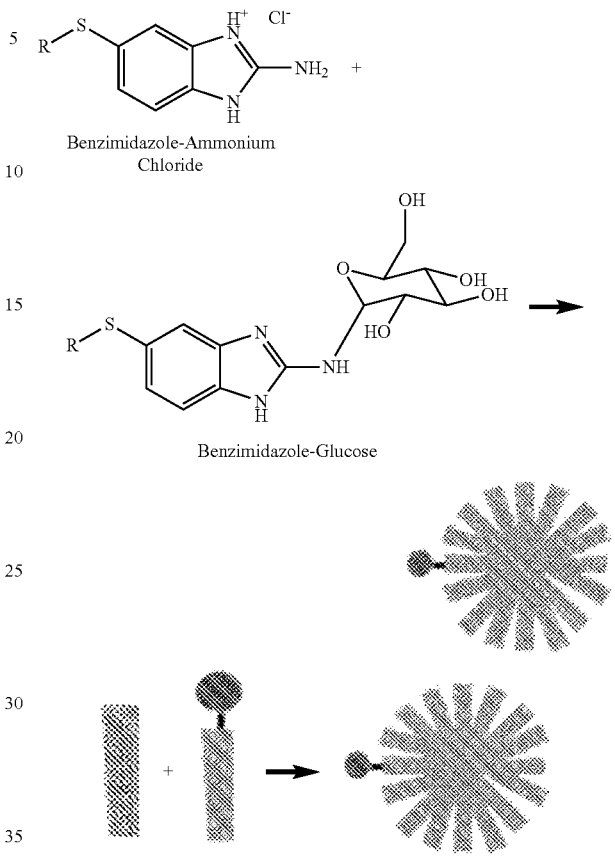

In one embodiment, the benzimidazole-ammonium compound represented by the chemical formula 1b or 2b above may be prepared as a result of reaction of a 2-aminobenzimidazole compound of chemical formula 1a or 2a hereunder with acids.

[Chemical formula 1a]

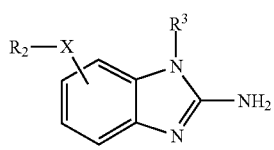

[Chemical formula 2a]

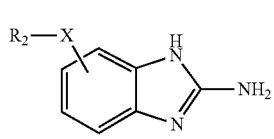

Wherein, $R_2$, $R_3$ and X are the same as those defined above.

Any substance that provides a hydrogen ion ($H^+$) may be used as the acid.

Reaction formula 2 hereunder may be presented as an example of a preparation method of the benzimidazole-ammonium compound used for preparation of a micelle according to the disclosure.

15

[Reaction formula 2]

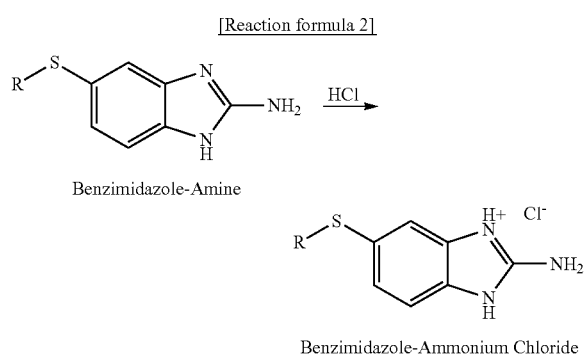

In one embodiment, the benzimidazole-carbohydrate conjugate compound may be obtained as a result of reaction of the 2-aminobenzimidazole compound of chemical formula 1a or 2a above with a carbohydrate, to form an imine bond.

In one embodiment, a substituent enabling an imine reaction, in the 2-aminobenzimidazole compound of chemical formula 1a, may be protected or shielded in advance.

Reaction formula 3 hereunder may be presented as an example of a preparation method of the benzimidazole-carbohydrate conjugate compound used for preparation of a micelle according to the disclosure.

Reaction formula 3 shows a reaction in which a D-glucose unit bonds to a 2-amino group of 6-alkylthio-2-aminobenzimidazole that is a precursor of albendazole or fenbendazole.

[Reaction formula 3]

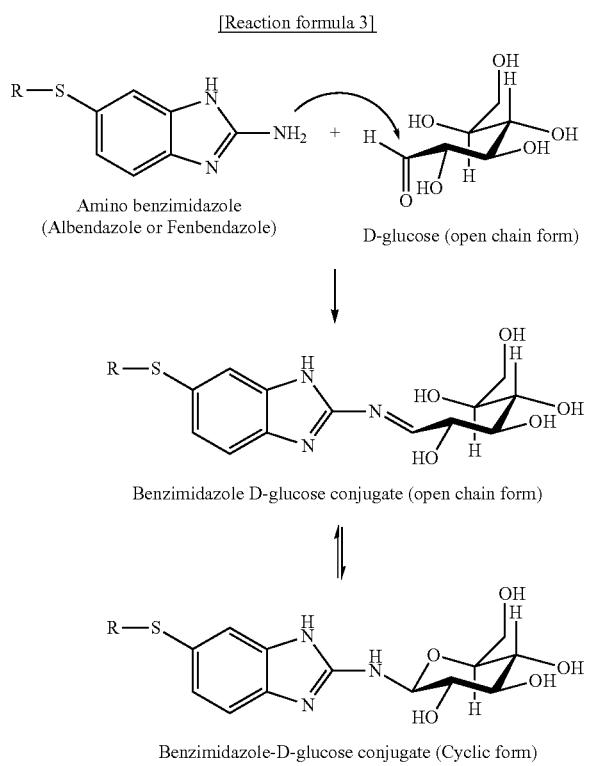

In reaction formula 3, an imine bond is formed as a result of reaction of the 2-amino group of the aminobenzimidazole with the aldehyde group of the D-glucose (an open chain form) such that the benzimidazole-carbohydrate conjugate compound, i.e., a benzimidazole-D-glucose (an open chain form) conjugate compound may be prepared.

The benzimidazole-D-glucose (an open chain form) conjugate compound may be converted to a cycle-form benzimidazole-D-glucose that is thermodynamically reliable.

Reaction formula 4 hereunder may be presented as another example of a preparation method of the benzimidazole-carbohydrate conjugate compound used for preparation of a micelle according to the disclosure.

Reaction formula 4 shows that a D-glucose unit bonds to the 2-amino group of the 6-alkylcarbonyl-2-aminobenzimidazole which is a precursor of flubendazole or mebendazole.

[Reaction formula 4]

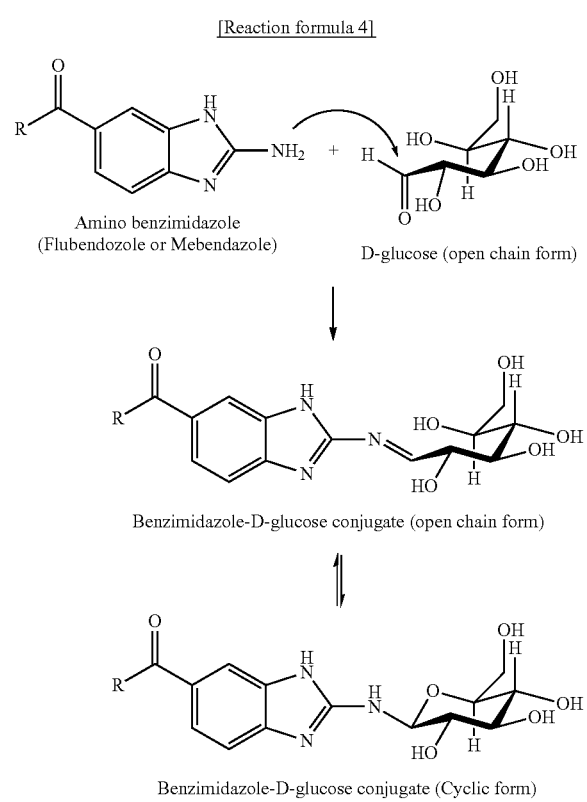

In reaction formulas 3 and 4, the resultant benzimidazole-carbohydrate conjugate compound may be isolated and/or refined using an ordinary method, and then ascertained using a spectroscopic method (e.g., $^1$H-NMR) and the like.

(3) Pharmacological Effect and Use of Micelle Comprising Benzimidazole-Carbohydrate Conjugate Compound The third objective of the present disclosure is to provide a pharmaceutical composition or a pharmacological composition of a micelle containing the benzimidazole-carbohydrate conjugate compound of chemical formula 1 above.

In one embodiment, a pharmaceutical composition, in which the micelle comprising the benzimidazole-carbohydrate conjugate compound illustrated in chemical formula 1 suppresses formation of microtubules and absorption of carbohydrates, preferably, sugar compounds comprising glucose, may be provided. That is, when the micelle is absorbed into cancer cells and virally infected cells, the micelle may suppress formation of microtubules and absorption of carbohydrates or sugar compounds comprising glucose.

In one embodiment, a pharmaceutical composition, in which the micelle comprising the benzimidazole-carbohydrate conjugate compound illustrated in chemical formula 1 shows an anticancer activity or an antiviral activity, may be provided. That is, the micelle may be selectively absorbed into cancer cells and virally infected cells that form more GLUT channels than normal cells, at a high rate, and show anticancer efficacy and antiviral efficacy.

In one embodiment, a pharmaceutical composition, in which the micelle comprising the benzimidazole-carbohydrate conjugate compound illustrated in chemical formula 1 is selectively absorbed through GLUT channels rather than cell membranes, may be provided.

In the disclosure, an albendazole-glucose (Al-G) compound, which is one of the benzimidazole-carbohydrate conjugate compounds, may be prepared in a way that glucose bonds to albendazole, the albendazole-glucose (Al-G) compound may be mixed with albendazole hydrochloride (Al—$NH^{3+}Cl^-$) to prepare a micelle, and the micelle may be absorbed through GLUT channels rather than cell membranes by the glucose included in the micelle when being absorbed into cells. This is one of the features of the subject matter of the disclosure. It is known that the GLUT channels are activated a lot in cancer cells or virally infected cells than in normal cells. According to a report, cancer cells form 1000 times more GLUT channels than normal cells. The micelle comprising the benzimidazole-carbohydrate conjugate compound according to the disclosure may be intensively absorbed into cancer cells and virally infected cells in which GLUT channels are activated than in normal cells (see L. Quan et al./Journal of Molecular Structure 1203 (2020) 127361).

It is known that tubulin in each cell is polymerized to form microtubules. A concentration of tubulin in each cell is about 5 uM (Biomolecules 2019, 9, 86; doi:10.3390/biom9030086), and to suppress the process in which tubulin is polymerized to microtubules, large amounts of drugs need to be absorbed for a short period of time. However, when the benzimidazole-carbohydrate conjugate compound is absorbed as a mono substance rather than a micelle, it is difficult to absorb large amounts of drugs for a short period of time. Thus, sufficient efficacy may not be ensured.

The micelle comprising the benzimidazole-carbohydrate conjugate compound according to the disclosure may help to intensively absorb large amounts of drugs into cancer cells and virally infected cells in which GLUT channels are activated than in normal cells, to show efficacy within a short period of time.

The suppression of the formation of microtubules may result in the suppression of the production of GLUT channels and the prevention of the absorption of glucose. Accordingly, the proliferation of cancer cells or the proliferation of viruses in virally infected cells may be significantly suppressed. Thus, the immune system in the body is known to attack the cancer cells or the virally infected cells, the proliferation of which is suppressed, and to produce anticancer and antiviral effects.

Figure 7:
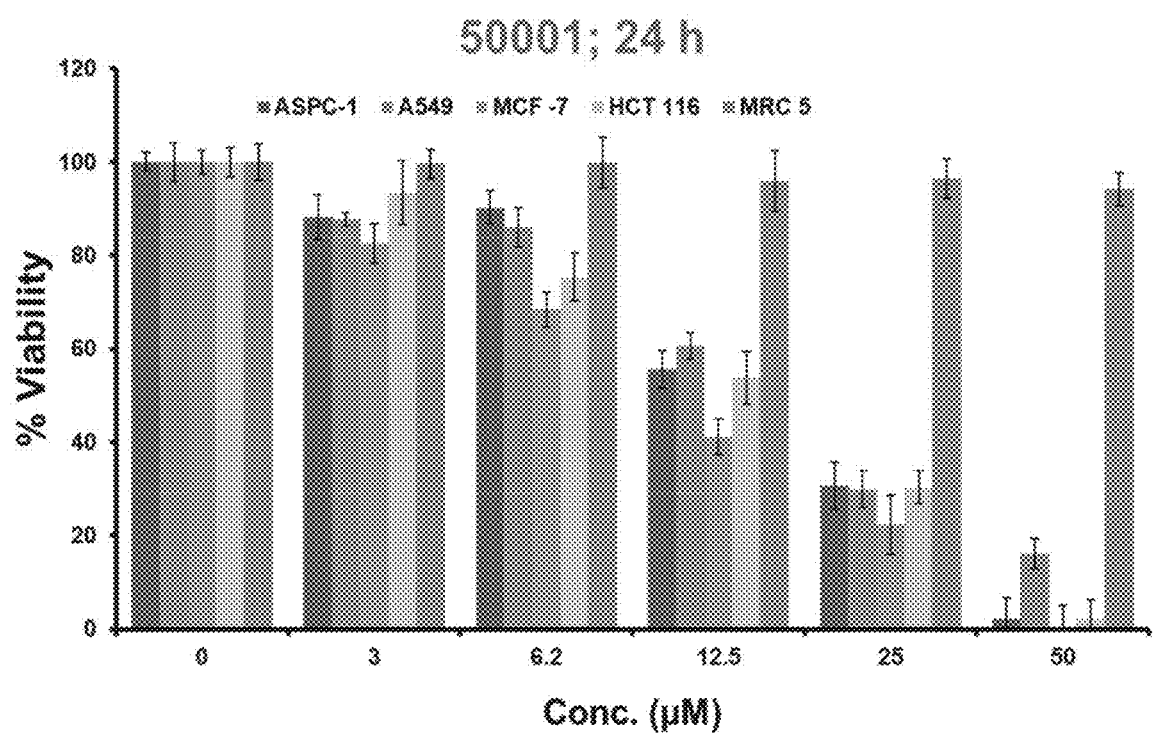
FIG. 7 is a graph showing viability in cancer cells and normal cells, depending on concentrations of micelle 50001 in one embodiment.
Figure 8:
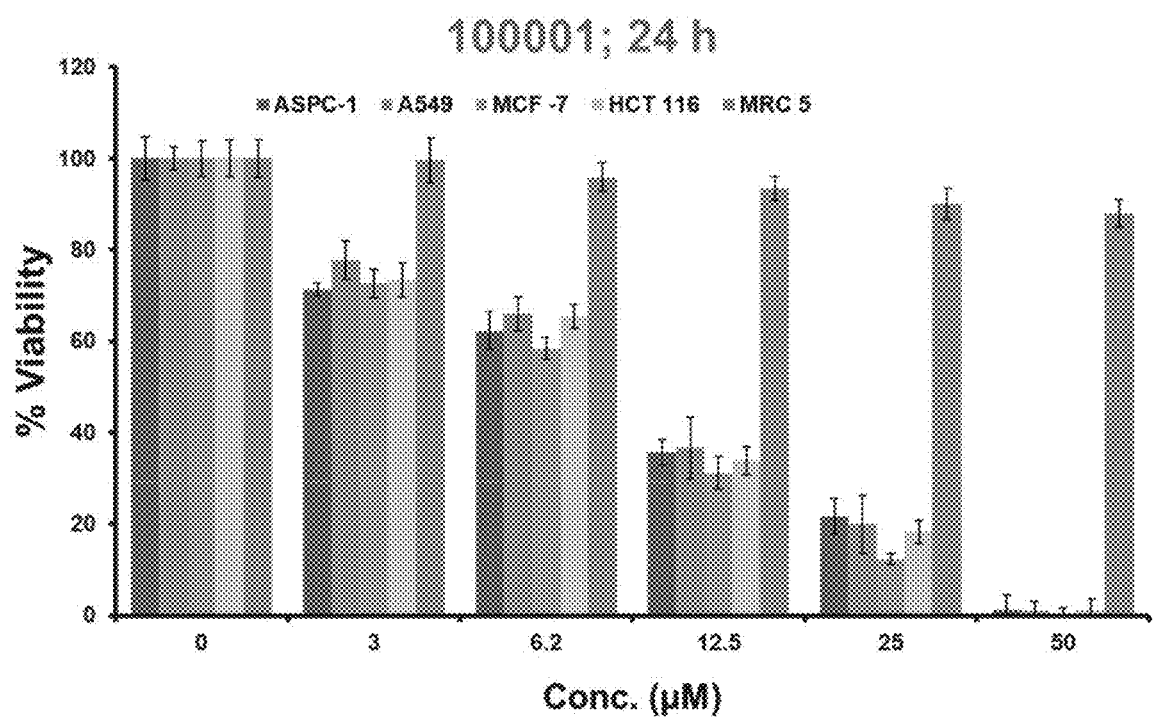
FIG. 8 is a graph showing viability in cancer cells and normal cells, depending on concentrations of micelle 100001 in one embodiment.
Figure 9:
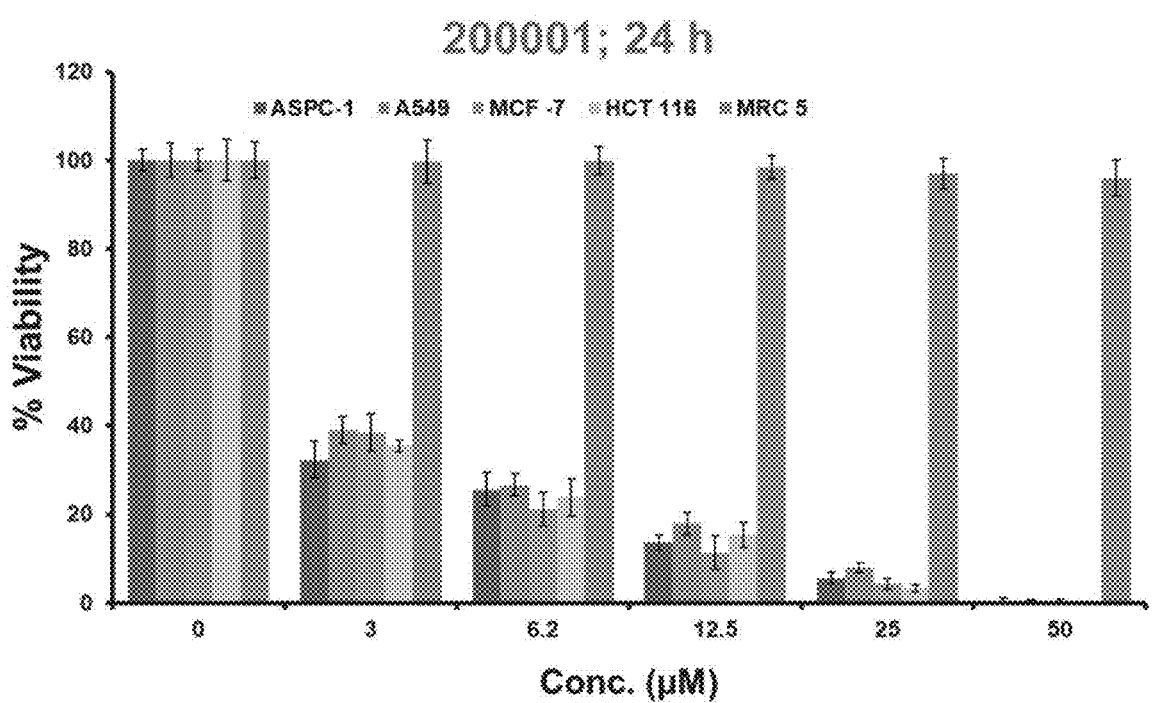
FIG. 9 is a graph showing viability in cancer cells and normal cells, depending on concentrations of micelle 200001 in one embodiment.

In one embodiment, the micelle, which is prepared using the 2-amino aminobenzimidazole hydrochloride produced by bonding hydrochloric acid (HCl) to the 2-aminobenzimidazole compound in chemical formula 1a and using the benzimidazole-carbohydrate conjugate compound in chemical formula 1, may be absorbed through GLUT channels rather than cell membranes. Referring to FIGS. 7, 8 and 9, breast cancer cells, lung cancer cells, colorectal cancer cells, and pancreatic cancer cells totally died within 24 hours. Under the same conditions, normal cells were rarely affected by the michelle.

The antiviral activity of the micelle comprising the benzimidazole-carbohydrate conjugate compound in chemical formula 1 according to the disclosure is described as follows.

Viruses are smaller than bacteria, are tiny particles (an average of 0.1 um or less) too tiny to be filtered through a bacterial filter (0.22 um), has nucleic acid (DNA or RNA) and a small number of proteins as a substance essential to life, and are living things dependent on hosts to live. When a human is infected by a virus, the virus may cause a virus-induced disease in the human body.

Most of the viruses have different features from those of bacteria, and a proliferation of the viruses is not suppressed by ordinary antibiotics. Drugs as a treating agent for a virus-induced disease are referred to as antiviral agents which weaken or remove actions of viruses having infected the human body, and viral infections needs to be treated by an antiviral agent since they are hardly treated by existing antibiotics.

Antiviral agents, developed and currently used, suppress a proliferation of viruses, i.e., a speed of a proliferation of viruses in cells infected by the viruses, to suppress an increase in the number of the cells infected by the viruses, to a degree that the immune system in the body attacks and removes the cells infected by the viruses.

Antiviral agents for suppressing a proliferation of viruses are drugs that interfere with a specific step during a proliferation of viruses in cells to suppress the proliferation of the viruses for treatment.

Antiviral agents can be categorized into agents for the flue, herpes, hepatitis B, hepatitis C, AIDS, and the like, based on conditions to be treated, and can be used to treat a variety of conditions, based on features of the agents.

Antiviral agents for treating the flu include Tamiflu®, RELENZA ROTADISK®, Peramiflu®, and the like that are used to treat viral infections such as influenza A and influenza B.

Antiviral agents for treating herpes include Zovirax®, Valtrex®, Famvir®, Ocufridine® and the like that are used to treat herpes simplex virus (HSV) infection and varicella zoster virus (VZV) infection.

Antiviral agents for treating hepatitis C can delay progression of the disease by suppressing a proliferation of hepatitis C viruses. Interferon injections for improving the immune system have been used together with ribavirin for a long time, to treat hepatitis C. Recently, direct acting antivirals (DAA) have been developed, and hepatitis C can be treated only using drugs that are taken orally. The agents include Viramid®, Exviera®, Sovald®, Daklinza®, Harvoni®, and the like.

In cocktail therapy, three or more antiviral agents are taken by an AIDS patient to delay progression of the disease by suppressing a proliferation of human immunodeficiency viruses (HIV) and are used to treat the disease while preventing development of tolerance, and the three or more antiviral agents include Combivir®, Kivexa®, Truvada®, Intelence® and the like.

Other antiviral agents strengthen or adjust a human's immune responses to suppress a proliferation of viruses, and include Roferon A®, Intron A®, Pegasys®, Aldara®, and the like that are substances produced and secreted in immune cells due to infection, and producing antiviral effects and having the ability to adjust immunity (see Korea Pharmaceutical Information Center).

However, a small number of antiviral agents and a few sorts of antiviral agents, capable of successfully treating viral infections, have been developed so far. Thus, the treatment of viral infections depends largely on the immune function of a patient.

Thus, there is a growing need for drugs that can suppress a proliferation of viruses by suppressing a speed of the proliferation of the viruses in cells infected by the viruses to suppress an increase in the number of the cells infected by the viruses, such that the immune system in the body attacks the cells infected by the viruses to the degree that the cells infected by the viruses are removed.

The micelle comprising the benzimidazole-carbohydrate conjugate compound according to the present disclosure is absorbed only into cancer cells and virally infected cells rather than normal cells, and then a benzimidazole compound derivative included in the micelle interferes with formation of microtubules, prevents cell division, and blocks absorption of carbohydrates comprising glucose that is an energy source of cells, resulting in deaths of the cancer cells and virally infected cells effectively. This is one of the advantages in the present disclosure.

Thus, the micelle comprising the benzimidazole-ammonium compound and the benzimidazole-carbohydrate conjugate compound according to the present disclosure can be intensively absorbed into cancer cells and virally infected cells, thereby minimizing toxicity affected on normal cells, and can be used to treat cancer and viral infections as anticancer compounds and antiviral compounds.

Hereunder, the subject matter of the present disclosure is described hereunder with reference to embodiments. However, the embodiments described hereunder are provided for detailed description of the subject matter of the disclosure. The scope of the disclosure should not be construed as being limited to the following embodiments, and the following embodiments can be properly changed and modified by one skilled in the art within the scope of the disclosure.

Embodiments

<Embodiment 1> Preparation of Albendazole-Ammonium (Al—$NH_3^+$) Compound

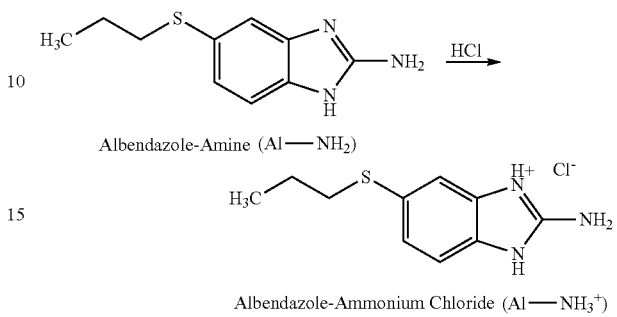

An Al—$NH_3$ compound is prepared by adding hydrochloric acid (HCl) to Al—$NH_2$, using methods described hereunder.

1) Put 5 g of Al—$NH_2$ (molecular weight: 207 g/mol) and 30 ml of acetone in a 100 ml single-neck round-bottom flask and stir the same in an ice bath for 20 minutes.
2) Put 4.23 g of NaCl (molecular weight: 58.44) in a two-neck round-bottom flask, close one of the two necks with a rubber cap, and install a valve connector connected with a rubber tube in the other of the two necks, connect a glass pipette at an end of the rubber tube connected with the valve connector, and submerge the glass pipette in the acetone solution of 1) to allow HCL gas to come out.
3) Add 3.9 ml of sulfuric acid to the round-bottom flask containing NaCl of 2) and then heat the same in a heating bath for 15 minutes.
4) When the color of the acetone solution turns from brown to purple, stir for 5 minutes in a state in which the heating stops, and filter the acetone solution with a filter.
5) Remove the filtered acetone solvent under a reduced pressure, and then obtain 5.8 g of a white crystalline Al—$NH_3^+$ compound (an yield of 98%).

<Embodiment 2> Preparation of Benzimidazole-Carbohydrate Conjugate Compound

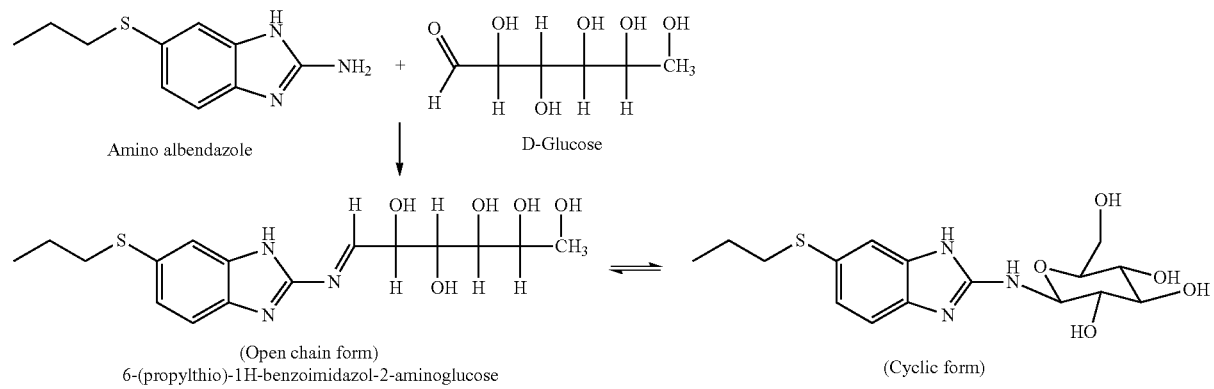

Embodiment 2-A: Albendazole-glucose conjugate compound

Based on a reaction formula above, an albendazole-glucose conjugate compound was prepared, and a document (Gokhale, Kearney, and Kirsch, AAPS PharmSciTech, Vol. 10, No. 2, June 2009) was referred to for reaction procedures and conditions.

To prepare a reaction mixture, 1.2 mM of aminoalbendazole (CAS #80983-36-4; Drug name: Albendazole amine) and 0.5 M of glucose were added to a hydrochloric acid solution (pH 3.45), and the reaction mixture reacted in a Teflon-coated rubber-cap glass vial at 40±1° C. and were diluted with an acetate buffer solution (0.5 M; pH 5.8). Then the reaction ended.

The solvent was removed, albendazol-glucode conjugate compound was purified using dichloromethane and 10% of methanol, based on column chromatography, and the albendazole-glucose conjugate compound was obtained at an yield of 62%.

The product was analyzed with a $^1$H-NMR spectrum to ascertain the production of the albendazole-glucose conjugate compound (FIG. 13; FIG. 17).

Embodiment 2-B: Fenbendazole-glucose conjugate compound

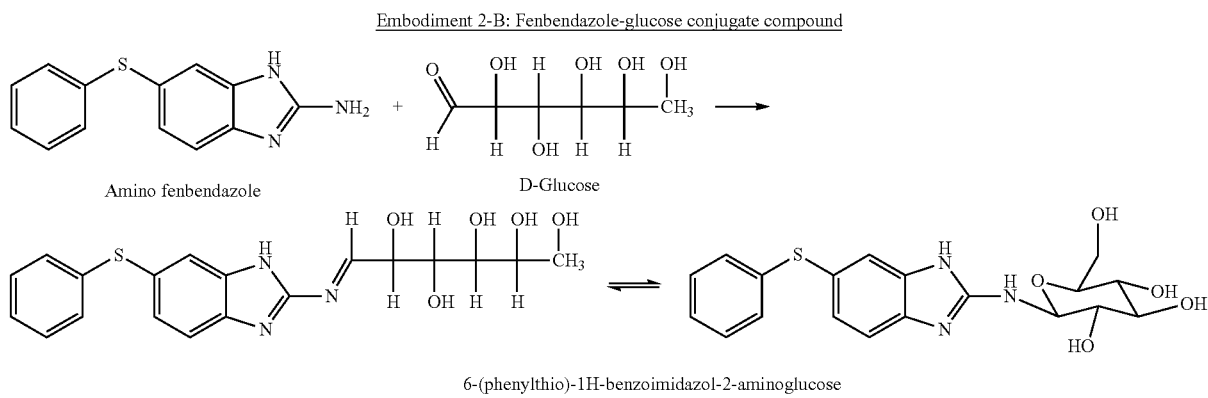

Except aminofenbendazole (CAS #1448346-29-9; a hydrochloride form) was used instead of aminoalbendazole, the procedures of embodiment 1-A were performed in the same way, and a fenbendazole-glucose conjugate compound was obtained as a benzimidazole-carbohydrate conjugate compound at an yield of 66%.

The product was analyzed with a $^1$H-NMR spectrum to ascertain the production of the fenbendazole-glucose conjugate compound (FIG. 14; FIG. 18).

Embodiment 2-C: Flubendazole-glucose conjugate compound

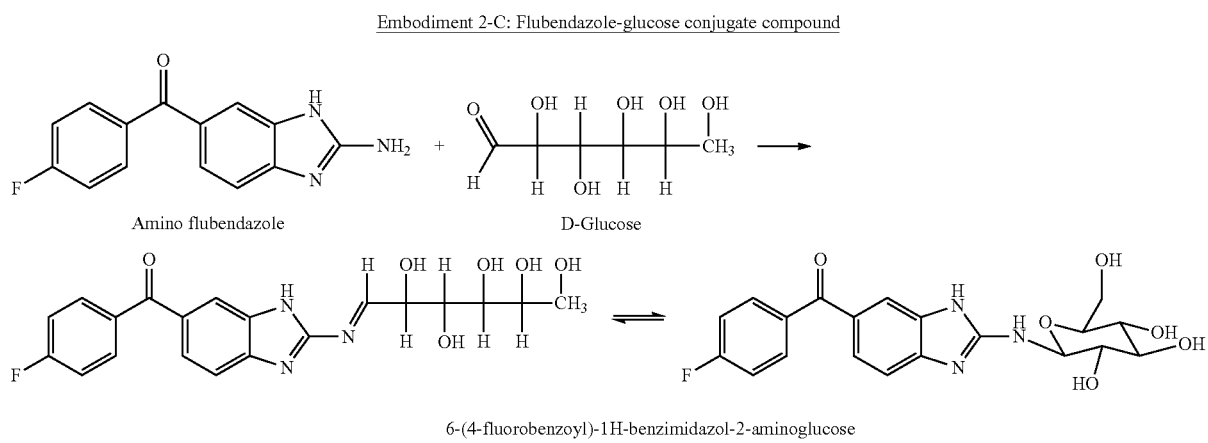

Based on a reaction formula above, a flubendazole-glucose conjugate compound was prepared, and a document (Gokhale, Kearney, and Kirsch, *AAPS PharmSciTech*, Vol. 10, No. 2, June 2009) was referred to for reaction procedures and conditions.

To prepare a reaction mixture, 1.2 mM of aminoflubendazole (CAS #82050-13-3; Drug name: 2-aminoflubendazole) and 0.5 M of glucose were added to a hydrochloric acid solution (pH 3.45), and the reaction mixture reacted in a Teflon-coated rubber-cap glass vial at 40±1° C. and were diluted with an acetate buffer solution (0.5 M; pH 5.8). Then the reaction ended.

The solvent was removed, flubendazole-glucose conjugate compound was purified using dichloromethane and 10% of methanol, based on column chromatography, and the flubendazole-glucose conjugate compound was obtained at an yield of 68%.

The product was analyzed with a $^1$H-NMR spectrum to ascertain the production of the flubendazole-glucose conjugate compound (FIG. 15; FIG. 19).

Embodiment 2-D: Mebendazole-glucose conjugate compound

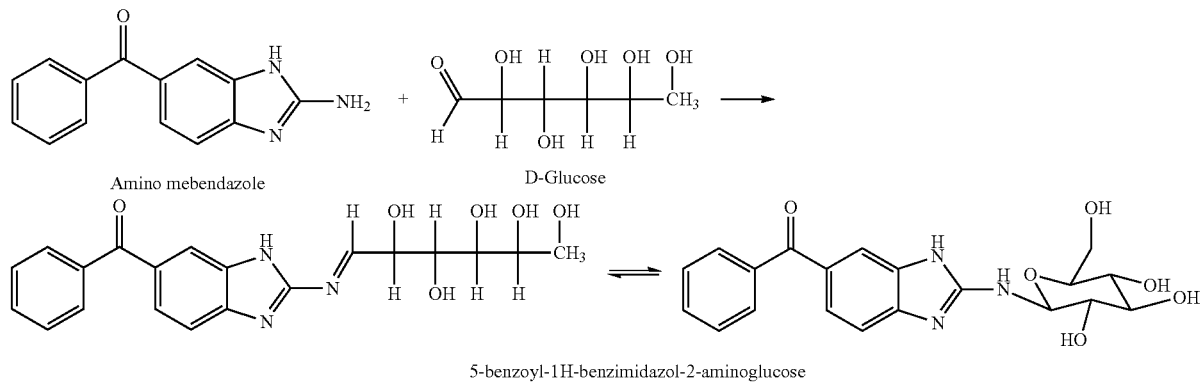

Except aminomebendazole (CAS #52329-60-9) was used instead of aminoflubendazole, the procedures of embodiment 2-C were performed in the same way, and a menbendazole-glucose conjugate compound was obtained at an yield of 66%.

The product was analyzed with a $^1$H-NMR spectrum to ascertain the production of the menbendazole-glucose conjugate compound (FIG. 16; FIG. 20).

<Embodiment 3> Preparation of Micelle Comprising Albendazole-Ammonium (Al—NH$_3^+$) Compound and Albendazole-Glucose (Al-G) Compound A micelle was prepared by mixing an Al—NH$_3^+$ compound that is a benzimidazole-ammonium compound with a Al-G compound that is a benzimidazole-carbohydrate compound.

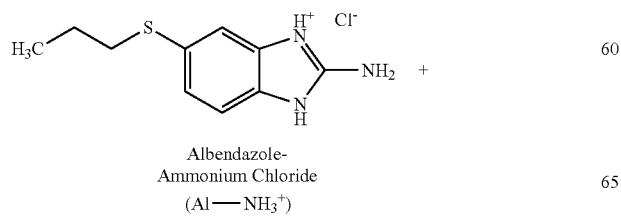

Albendazole-Ammonium Chloride
(Al—NH$_3^+$)

-continued

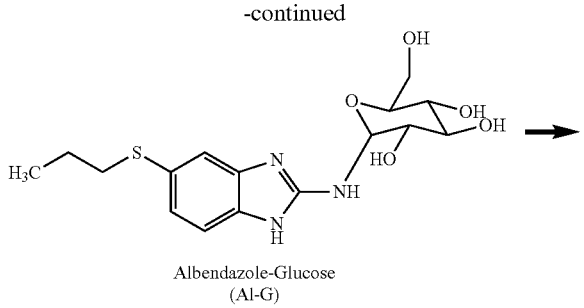

Albendazole-Glucose
(Al-G)

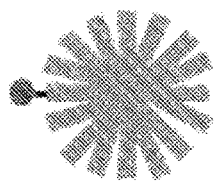

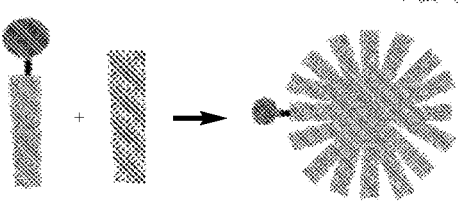

To prepare 200 mM of a stock solution, 100 mg of Al—NH$_3^+$ molecular weight. 243 g/mol) was melted in 2 ml of DMSO, and to prepare 200 mM of a stock solution, 100 mg of Al-G (molecular weight. 369 g/mol) was melted in 1.35 ml of DMSO. Six sorts of micelles were prepared by mixing the two solutions at ratios in table 1.

TABLE 1

| Name of micelles | Al—NH$_3^+$:Al—G (molar ratio) | Al—NH$_3^+$ stock solution (200 mM) | Al—G stock solution (200 mM) |
| --- | --- | --- | --- |
| 5001 | 5:1 | 200 ul | 40 ul |
| 10001 | 10:1 | 200 ul | 20 ul |
| 20001 | 20:1 | 200 ul | 10 ul |
| 50001 | 50:1 | 200 ul | 4 ul |
| 100001 | 100:1 | 200 ul | 2 ul |
| 200001 | 200:1 | 200 ul | 1 ul |

To prepare a solution to be injected to cells, 0.5 ml of each of the six sorts of mixtures in table 1 was mixed with 100 ml of a saline solution. The solution to be injected to cells was diluted at concentrations in table 2 and used for a test for inhibition of growth of cancer cell lines.

<Embodiment 4>
Preparation of micelle comprising albendazole-glucose (Al-G) compound

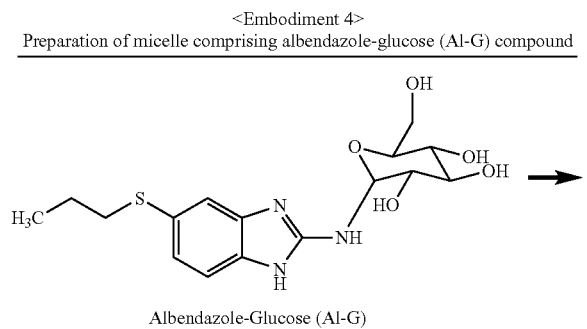

Albendazole-Glucose (Al-G)

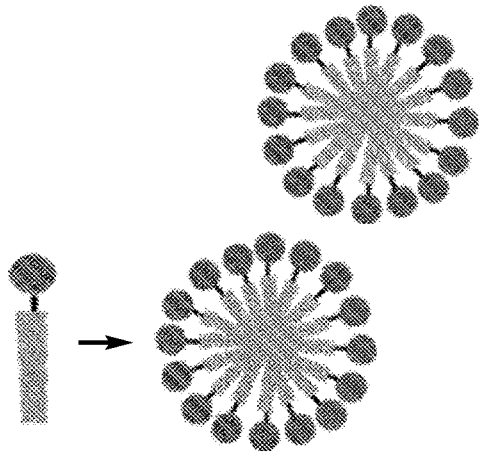

To prepare a 1000 uM solution for a cell test, a solution to be injected to cells, 0.5 ml of the 200 mM Al-G stock solution in table 1 was mixed with 100 ml of a saline solution. The solution for a cell test was diluted at the concentrations in table 2 and used for a test for inhibition of growth of cancer cell lines.

<Embodiment 5> Preparation of micelle comprizing albendazole-ammonium compound (Al—NH$_3^+$)

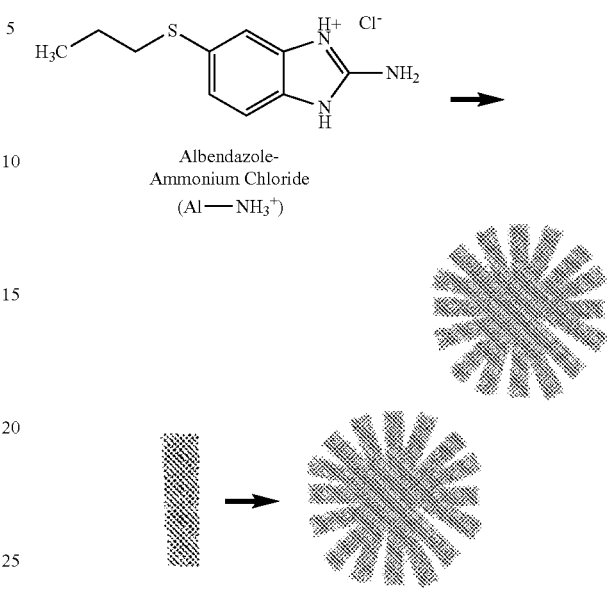

Albendazole-Ammonium Chloride (Al—NH$_3^+$)

To prepare a 1000 uM solution for a cell test, a solution to be injected to cells, 0.5 ml of the 200 mM Al—NH$_3$ stock solution in table 1 was mixed with 100 ml of a saline solution. The solution for a cell test was diluted at the concentrations in table 2 and used for a test for inhibition of growth of cancer cell lines.

<Embodiment 6> Test for Inhibition of Growth of Cancer Cell Lines

Pancreatic cancer cell lines ASPC-1, lung cancer cell lines A549, breast cancer cell lines MCF-7, and colorectal cancer cell lines HCT 116 of humans were distributed by Korean Cell Line Bank (KCLB, Seoul in Korea) and grown using culture media. Fetal bovine serum (FBS), 0.1 mM MEM nonessential amino acid (NEAA), 2 mM L-glutamine, and 1% of penicillin-streptomycin were treated with trypsin every two-three days in a humidified cell culture incubator containing 5% of CO$_2$ at 37° C. by using DMEM and a 10% culture flask according to guidelines provided by the KCLB, to subculture cells. The culture was incubated until it reached 80-90% confluence, and the cells continuously moved to the culture flask for a test of inhibition of growth of cancer cell lines.

The cancer cell lines (pancreatic cancer cell line ASPC-1, lung cancer cell line A549, breast cancer cell line MCF-7, and colorectal cancer cell line HCT 116) were seeded in 96 well-plates at about 7,000 cells per well. After 24 hours, each of the nine sorts of compounds in table 2 was added to the well under six concentration conditions and was incubated for 24 hours.

TABLE 2

| Compound | Concentration |
| --- | --- |
| Albendazole-ammonium (Al—NH$_3^+$) | 0 μM, 3 μM, 6.2 μM, 12.5 μM, 25 μM, 50 μM |

TABLE 2-continued

| Compound | Concentration |
|---|---|
| Albendazole-glucose conjugate (Al—G) | 0 μM, 3 μM, 6.2 μM, 12.5 μM, 25 μM, 50 μM |
| 5001 | 0 μM, 3 μM, 6.2 μM, 12.5 μM, 25 μM, 50 μM |
| 10001 | 0 μM, 3 μM, 6.2 μM, 12.5 μM, 25 μM, 50 μM |
| 20001 | 0 μM, 3 μM, 6.2 μM, 12.5 μM, 25 μM, 50 μM |
| 50001 | 0 μM, 3 μM, 6.2 μM, 12.5 μM, 25 μM, 50 μM |
| 100001 | 0 μM, 3 μM, 6.2 μM, 12.5 μM, 25 μM, 50 μM |
| 200001 | 0 μM, 3 μM, 6.2 μM, 12.5 μM, 25 μM, 50 μM |
| doxorubicin | 0 μM, 3 μM, 6.2 μM, 12.5 μM, 25 μM, 50 μM |

After the incubation, the culture medium was thrown away, and cell viability in each well was measured according to an instruction of the manufacturer, using a WST-8 cell viability assay kit (Quanti-Max™, BIOMAX).

The analysis used the principle that the dehydrogenase of living cells decomposes tetrazolium salt to generate formazan, and based on this, the living cells were quantitatively evaluated. Reduced formazan dye (formazan salt) is soluble in the cell culture medium, and the amount of formazan (formazan) was measured using the direct proportionality to the number of viable cells.

Figure 4:
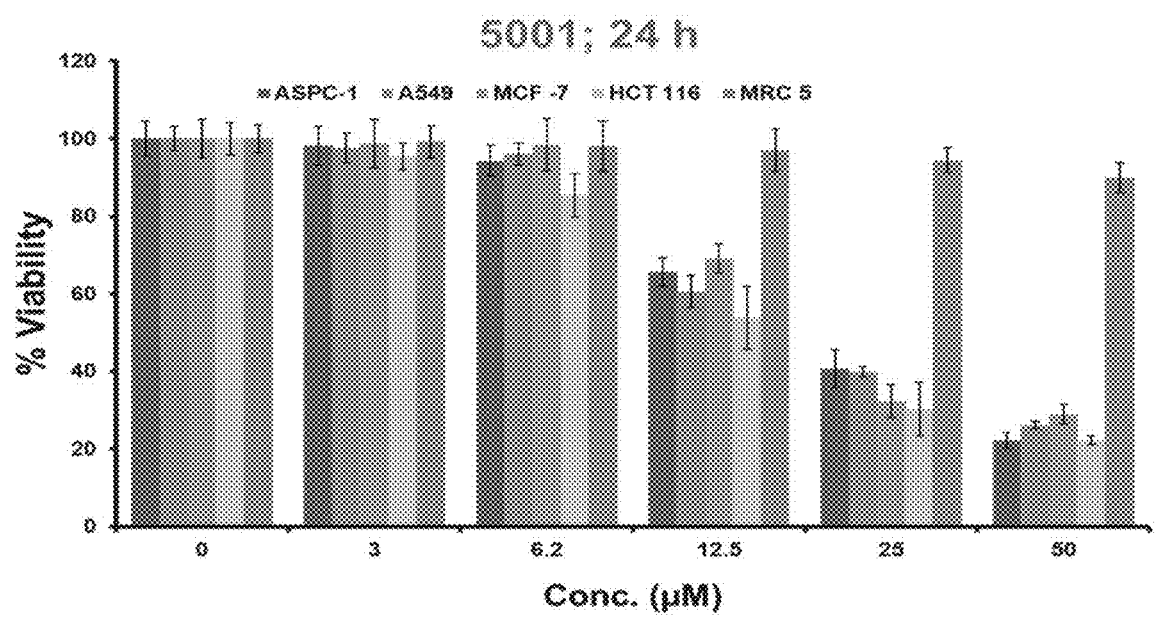
FIG. 4 is a graph showing viability in cancer cells and normal cells, depending on concentrations of micelle 5001 in one embodiment.
Figure 5:
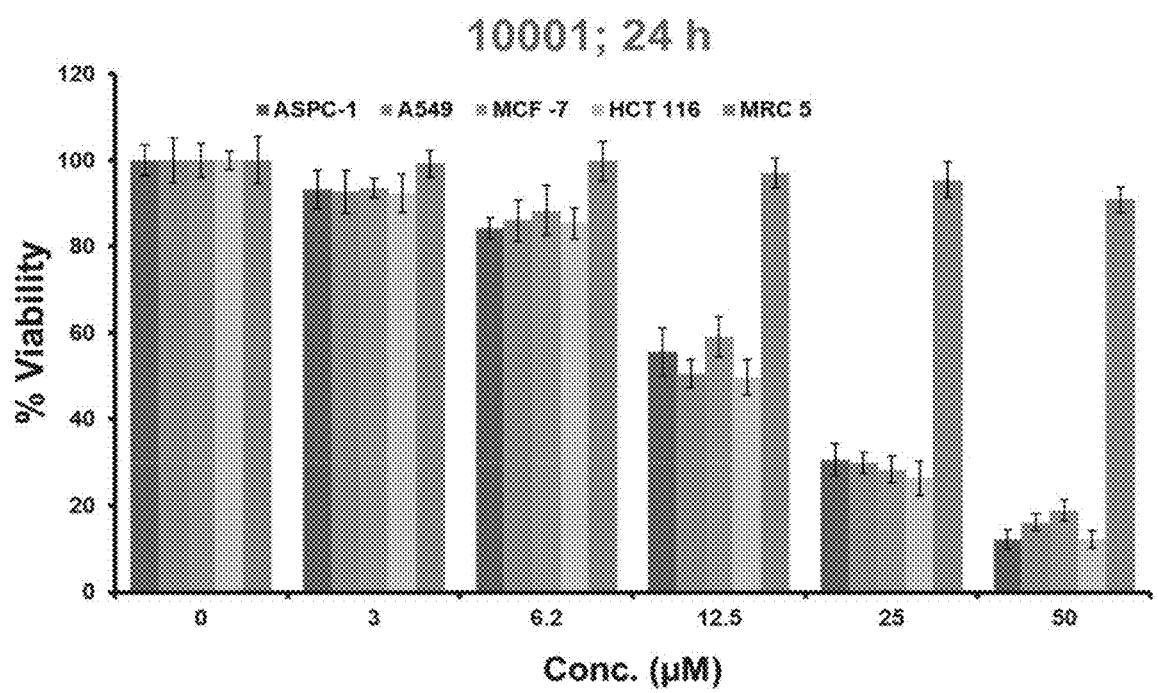
FIG. 5 is a graph showing viability in cancer cells and normal cells, depending on concentrations of micelle 10001 in one embodiment.
Figure 6:
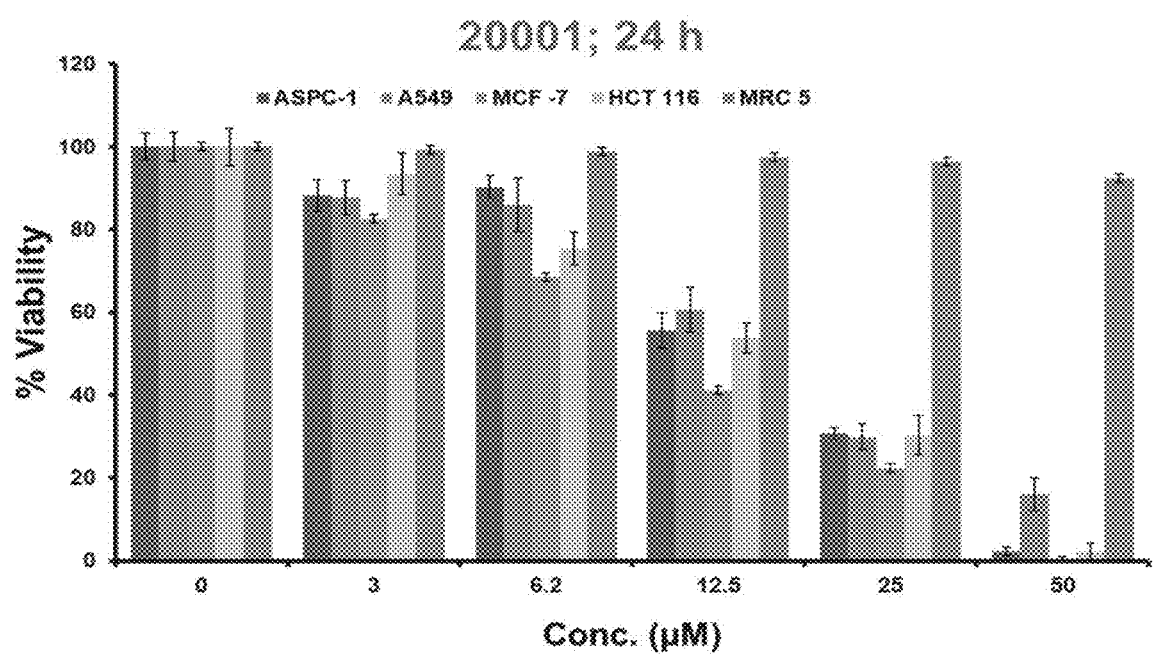
FIG. 6 is a graph showing viability in cancer cells and normal cells, depending on concentrations of micelle 20001 in one embodiment.
Figure 12:
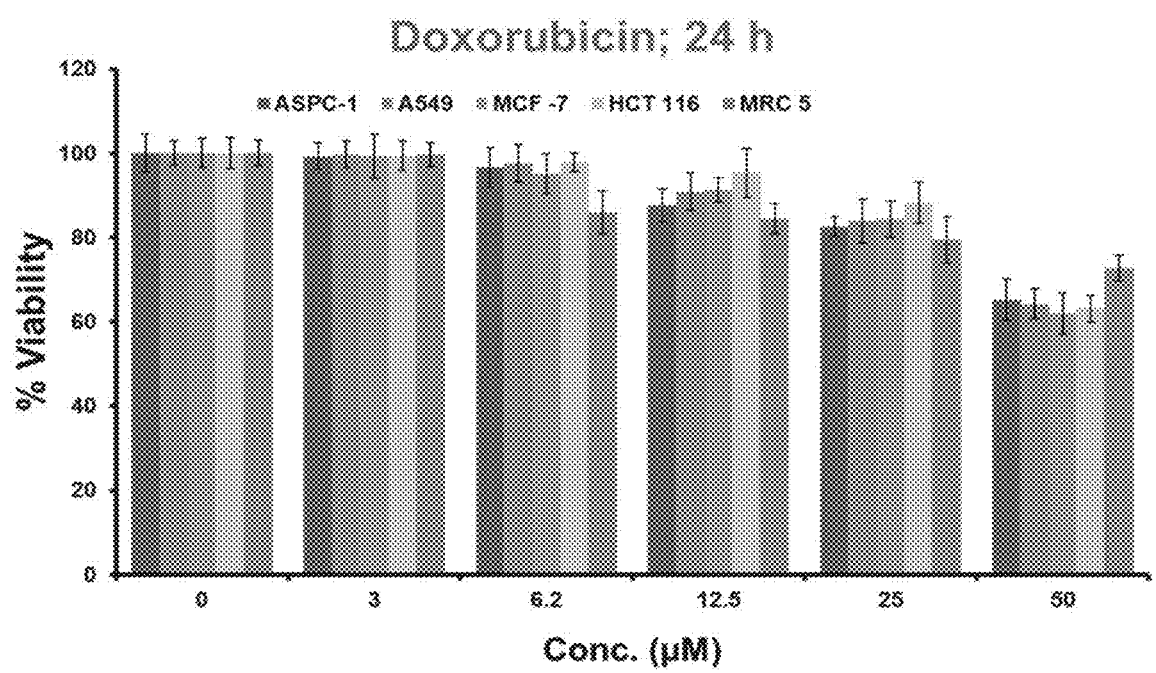
FIG. 12 is a graph showing viability in cancer cells and normal cells, depending on concentrations of a doxorubicin compound in the cancer cells and the normal cells.

Table 3, FIG. 4 and FIG. 12 show results of the test for inhibition of growth of the cancer cell lines described above.

In FIG. 12, doxorubicin is a drug approved by the FDA. When doxorubicin was injected at the same concentrations (Table 2) as concentrations of the micelle in one embodiment, 70% or greater of a total number of cancer cells remained within 24 hours.

Figure 10:
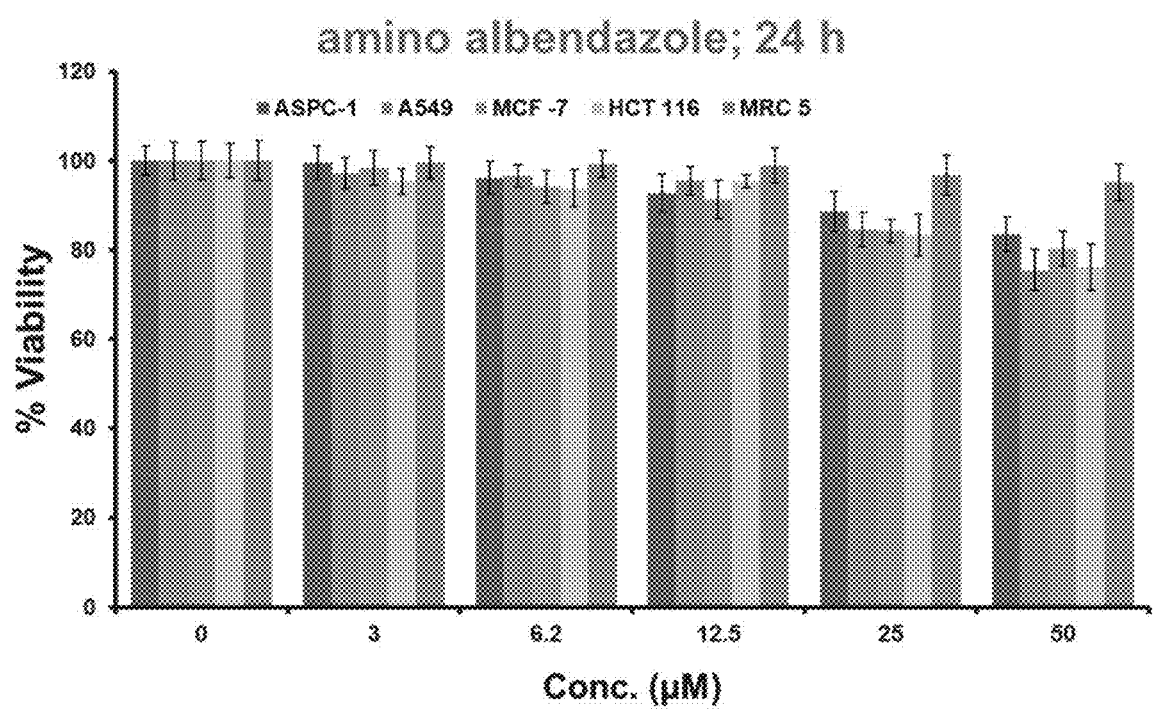
FIG. 10 is a graph showing viability in cancer cells and normal cells, depending on concentrations of the micelle comprising an albendazole-ammonium (Al—$NH_3^+$) compound in one embodiment.
Figure 11:
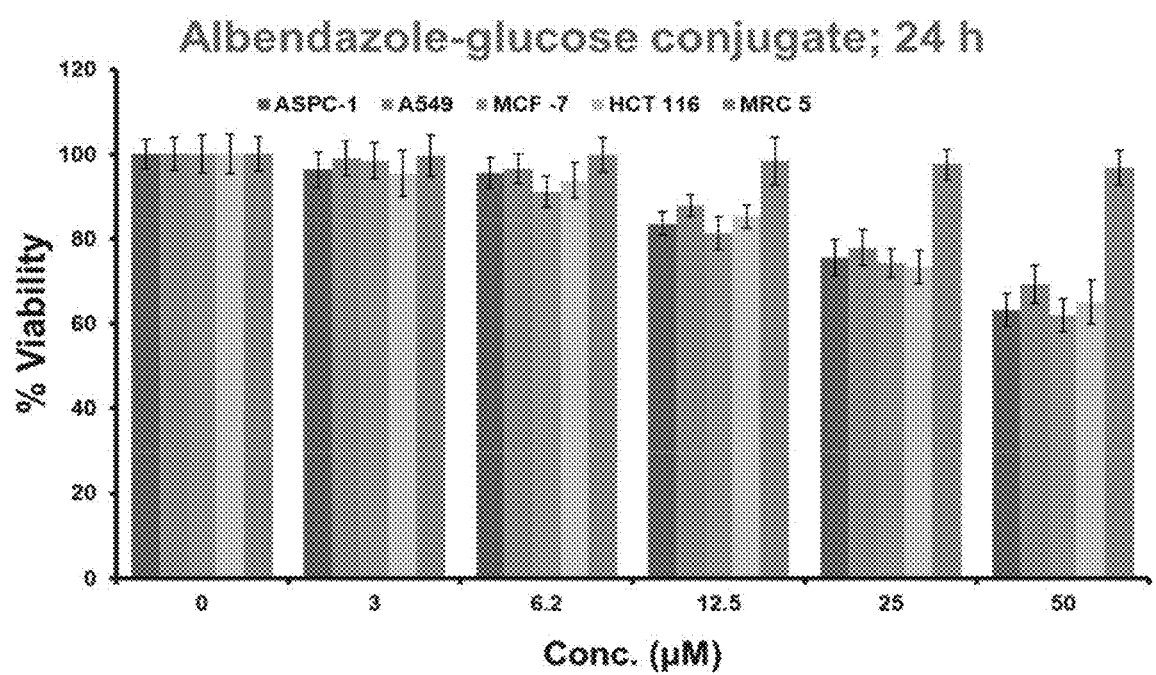
FIG. 11 is a graph showing viability in cancer cells and normal cells, depending on concentrations of the micelle comprising an albendazole-glucose (Al-G) compound in one embodiment.

Referring to FIGS. 10-11, when a micelle comprising the benzimidazole-ammonium single compound or a micelle comprising the benzimidazole-carbohydrate conjugate single compound was injected at the same concentrations (Table 2) as concentrations of the micelle comprising the benzimidazole-ammonium compound and the benzimidazole-carbohydrate conjugate compound, 70-90% or greater of a total number of cancer cells remained within 24 hours.

Referring to FIGS. 7, 8 and 9, when the micelle comprising the benzimidazole-ammonium compound and the benzimidazole-carbohydrate conjugate compound is injected at the same concentrations (Table 2) as concentrations of doxorubicin, the cancel cells died completely within 24 hours. In particular, the breast cancer cells, the lung cancer cells, the colorectal cancer cells, and the pancreatic cancer cells died completely within 24 hours, resulting in inhibition of growth of the cancer cell lines, while the normal cells were rarely affected by the micelle under the same conditions.

<Embodiment 7> Test for Toxicity on Normal Cell Lines

Normal lung cell lines MRC-5 were distributed by Korean Cell Line Bank (KCLB, Seoul in Korea) and grown using a complete culture medium. Fetal bovine serum (FBS), 0.1 mM MEM nonessential amino acid (NEAA), 2 mM L-glutamine, and 1% of penicillin-streptomycin were treated with trypsin every two-three days in a humidified cell culture incubator containing 5% of $CO_2$ at 37° C. by using DMEM and a 10% culture flask according to guidelines provided by the KCLB, to subculture cells. The culture was incubated until it reached 80-90% confluence, and the cells continuously moved to the culture flask for a test of inhibition of growth of cancer cell lines.

The normal cell lines (MRC-5) were seeded in 96-well plates at about 7,000 cells per well. After 24 hours, each of the nine sorts of compounds in table 2 was added to the well under six concentration conditions and was incubated for 24 hours.

After the incubation, the culture medium was thrown away, and cell viability in each well was measured according to an instruction of the manufacturer, using a WST-8 cell viability assay kit (Quanti-Max™, BIOMAX).

The analysis used the principle that the dehydrogenase of living cells decomposes tetrazolium salt to generate formazan, and based on this, the living cells were quantitatively evaluated. Reduced formazan dye (formazan salt) is soluble in the cell culture medium, and the amount of formazan (formazan) was measured using the direct proportionality to the number of viable cells.

Table 3, FIG. 4 and FIG. 12 show results of the test for toxicity on the normal cell lines described above.

Table 3 shows results of the test for inhibition of growth of the cancer cell lines and the test for toxicity on the normal cell lines relative to doxorubicin. The first column shows the results of the test for inhibition of growth of the cancer cell lines relative to doxorubicin, and an AAA rating denotes an excellent quality (one time or less), an AA rating denotes equality (1-2 times), an A rating denotes a slightly weak quality (3-5 times), a B rating denotes a weak quality (5-10 times), and a C rating denotes a very weak quality (10 times or more). The second column shows results of the test for toxicity on the normal cell lines relative to doxorubicin, and an AAA rating denotes no toxicity (1/30 times or less), an AA rating denotes almost no toxicity (1/10 times or less), an A rating denotes slight toxicity (1/3 times or less), a B rating denotes equality (1-2 times), and a C rating denotes high toxicity (10 times or more). In table 3 below, the micelles comprising the benzimidazole-ammonium compound and the benzimidazole-carbohydrate conjugate compound according to the present disclosure shows an excellent growth inhibition activity in the cancer cell lines, and shows no toxicity in the normal cell lines as a result of estimation of the effect of the compounds on the growth inhibition of the cancer cell lines and the toxicity on the normal cell lines.

TABLE 3

| Compound | Test for inhibition of growth of cancer cell line | Test for toxicity on normal cell line |
|---|---|---|
| Albendazole-ammonium ($Al-NH_3^+$) | C | AAA |
| Albendazole-glucose conjugate (Al—G) | C | AAA |
| 5001 | AAA | AAA |
| 10001 | AAA | AAA |
| 20001 | AAA | AAA |
| 50001 | AAA | AAA |
| 100001 | AAA | AAA |
| 200001 | AAA | AAA |

The embodiments of the micelle comprising the benzimidazole-carbohydrate conjugate compound, the preparation method thereof, the use thereof as an anticancer agent or an antiviral agent, according to the present disclosure, are described above. However, it is apparent that the embodiments can be modified in various different forms within the scope of the disclosure.

Thus, the scope of the disclosure should not be limited by the embodiments set forth herein, but be defined based on the accompanying claims and equivalents thereof.

The embodiments described above are provided as examples and are not limited, in all respects. Further, the scope of the disclosure should be defined by the accompanying claims rather than the detailed description, and all modifications and changes drawn from the meaning and scope of the claims and the equivalents thereof should be construed as being included in the scope of the disclosure.

What is claimed is:

1. A micelle comprising a benzimidazole-carbohydrate conjugate compound represented by the following chemical formula 1 and a benzimidazole-ammonium compound represented by the following chemical formula 1b:

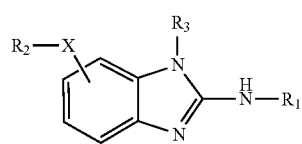

[Chemical formula 1]

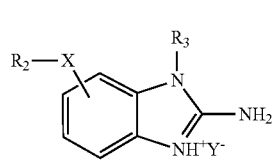

[Chemical formula 1b]

wherein, the —NH—$R_1$ moiety has one of the following structures:

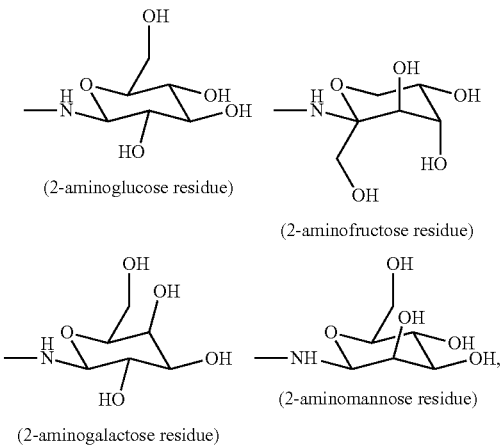

the benzimidazole moiety has one of the following structures:

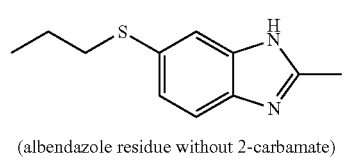

(albendazole residue without 2-carbamate)

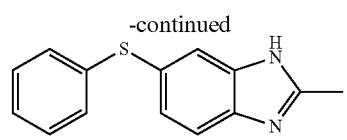

(febendazole residue without 2-carbamate)

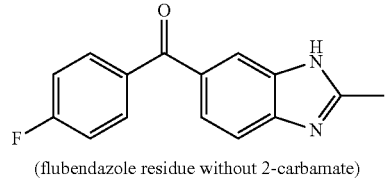

(flubendazole residue without 2-carbamate)

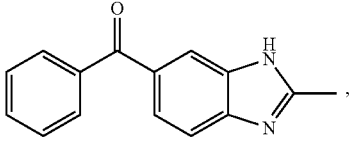

(mebendazole residue without 2-carbamate)

and $Y^-$ is a conjugate base of acid ($H^+$) and is selected from $Cl^-$, $Br^-$, $I^-$, $F^-$, $NO_3^-$, $CH_3COO^-$, $HCOO^-$, $HCO_3^-$, $CO_3^{2-}$, $H_2PO_4^-$, $HPO_4^{2-}$, $HSO_4^-$, $SO_4^{2-}$, or $ClO_4^-$.

2. The micelle of claim 1, wherein the micelle comprises one or more selected from a group consisting of 6-(propylthio)-1H-benzoimidazol-2-aminoglucose, 6-(propylthio)-1H-benzoimidazol-2-aminofructose, 6-(propylthio)-1H-benzoimidazol-2-aminogalactose, and 6-(propylthio)-1H-benzoimidazol-2-aminomannose, as an albendazole-D-carbohydrate conjugate compound;

6-(phenylthio)-1H-benzoimidazol-2-aminoglucose, 6-(phenylthio)-1H-benzoimidazol-2-aminofructose, 6-(phenylthio)-1H-benzoimidazol-2-aminogalactose, and 6-(phenylthio)-1H-benzoimidazol-2-aminomannose, as a fenbendazole-D-carbohydrate conjugate compound;

6-(4-fluorobenzoyl)-1H-benzimidazol-2-aminoglucose, 6-(4-fluorobenzoyl)-1H-benzimidazol-2-aminofructose, 6-(4-fluorobenzoyl)-1H-benzimidazol-2-aminogalactose, and 6-(4-fluorobenzoyl)-1H-benzimidazol-2-aminomannose, as a flubendazole-D-carbohydrate conjugate compound; and 6-benzoyl-1H-benzimidazol-2-aminoglucose, 6-benzoyl-1H-benzimidazol-2-aminofructose, 6-benzoyl-1H-benzimidazol-2-aminogalactose, and 6-benzoyl-1H-benzimidazol-2-aminomannose, as a mebendazole-D-carbohydrate conjugate compound.

3. The micelle of claim 1, wherein a molar ratio of the benzimidazole-ammonium compound to the benzimidazole-carbohydrate conjugate compound is 1:500-500:1.

4. The micelle of claim 1, wherein concentrations of a benzimidazole-ammonium compound and the benzimidazole-carbohydrate conjugate compound left in cells, into which the micelle is inserted, for 24 to 72 hours are kept higher than concentrations of the benzimidazole-ammonium compound and the benzimidazole-carbohydrate conjugate compound discharged from the cells into which the micelle is inserted, after the micelle is inserted into the cells.

5. A preparation method of a micelle, comprising mixing a benzimidazole-carbohydrate conjugate compound represented by the following chemical formula 1 with a benzimidazole-ammonium compound represented by the following chemical formula 1b:

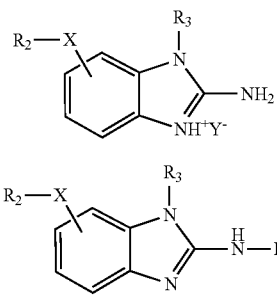

[Chemical formula 1b]

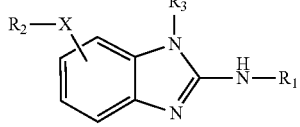

[Chemical formula 1]

wherein, the —NH—R$_1$ moiety has one of the following structures:

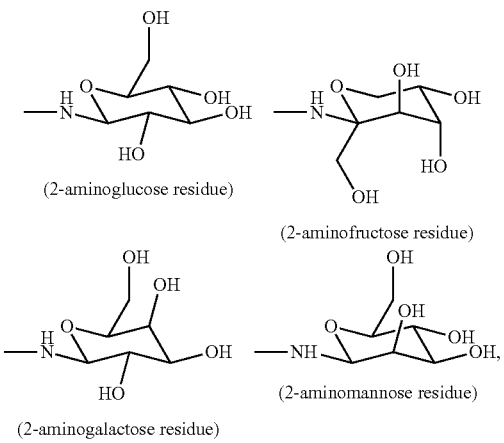

the benzimidazole moiety has one of the following structures:

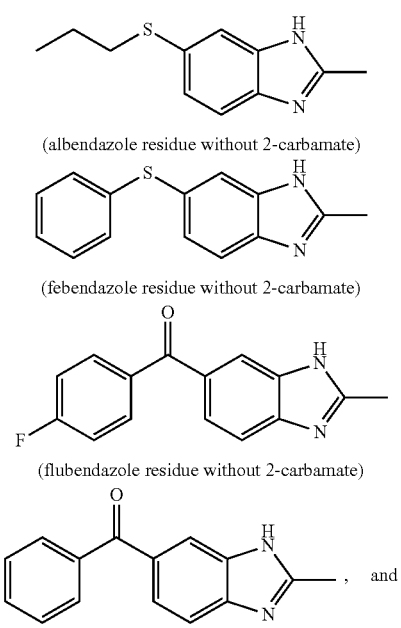

Y$^-$ is a conjugate base of acid (H$^+$) and selected from Cl$^-$, Br$^-$, I$^-$, F$^-$, NO$_3^-$, CH$_3$COO$^-$, HCOO$^-$, HCO$_3^-$, CO$_3^{2-}$, H$_2$PO$_4^-$, HPO$_4^{2-}$, HSO$_4^-$, SO$_4^{2-}$, or ClO$_4^-$.

6. The preparation method of claim 5 wherein the benzimidazole-ammonium compound represented by chemical formula 1b is prepared as a result of reaction of a 2-aminobenzimidazole compound of the following chemical formula 1a with acids:

[Chemical formula 1a]

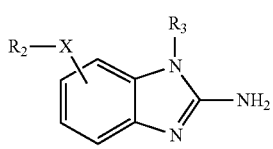

wherein, the benzimidazole moiety has one of the following structures:

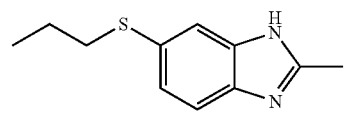

(albendazole residue without 2-carbamate)

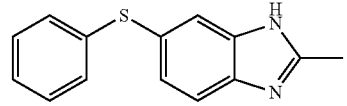

(febendazole residue without 2-carbamate)

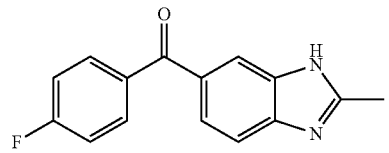

(flubendazole residue without 2-carbamate)

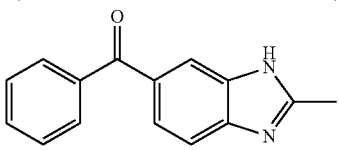

(mebendazole residue without 2-carbamate)

7. The preparation method of claim 5, wherein the benzimidazole-carbohydrate conjugate compound represented by chemical formula 1 is obtained as a result of reaction of the 2-aminobenzimidazole compound of the following chemical formula 1a with carbohydrates to form an imine bond:

[Chemical formula 1a]

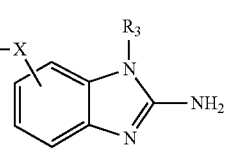

wherein, the benzimidazole moiety has one of the following structures:

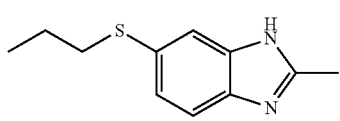

(albendazole residue without 2-carbamate)

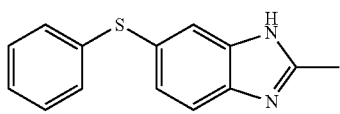

(febendazole residue without 2-carbamate)

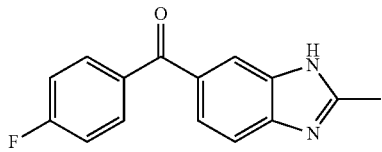

(flubendazole residue without 2-carbamate)

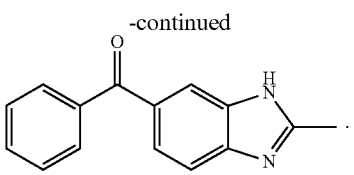

(mebendazole residue without 2-carbamate)

8. The preparation method of claim 7, wherein a substituent enabling an imine reaction, in the 2-aminobenzimidazole compound of chemical formula 1a, is protected or shielded in advance.

9. A pharmaceutical composition, containing the micelle of claim 1.

10. The pharmaceutical composition of claim 9, wherein the pharmaceutical composition suppresses formation of microtubules and absorption of carbohydrates.

11. The pharmaceutical composition of claim 9, wherein the pharmaceutical composition shows anticancer or antiviral activity.

12. The pharmaceutical composition of claim 9, wherein the pharmaceutical composition is absorbed through glucose transporter (GLUT) channels.

* * * * *